(12) United States Patent
Ellsworth et al.

(10) Patent No.: US 7,326,706 B2
(45) Date of Patent: Feb. 5, 2008

(54) PYRAZINE MODULATORS OF CANNABINOID RECEPTORS

(75) Inventors: Bruce A. Ellsworth, Princeton, NJ (US); Chongqing Sun, East Windsor, NJ (US); Annapurna Pendri, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 339 days.

(21) Appl. No.: 10/917,199

(22) Filed: Aug. 12, 2004

(65) Prior Publication Data

US 2005/0054659 A1 Mar. 10, 2005

Related U.S. Application Data

(60) Provisional application No. 60/495,807, filed on Aug. 15, 2003.

(51) Int. Cl.
*A01N 43/64* (2006.01)
*A61K 31/53* (2006.01)
*A61K 31/4965* (2006.01)
*C07D 401/00* (2006.01)
*C07D 241/02* (2006.01)

(52) U.S. Cl. ............... 514/241; 514/242; 514/255.05; 514/255.06; 544/180; 544/182; 544/295; 544/405; 544/406

(58) Field of Classification Search ............... None
See application file for complete search history.

(56) References Cited

U.S. PATENT DOCUMENTS

| 2,479,442 A | | 8/1949 | Weijlard et al. ............ 260/250 |
|---|---|---|---|
| 3,313,813 A | * | 4/1967 | Cragoe, Jr. ................. 260/250 |
| 3,761,477 A | | 9/1973 | Schwartz et al. ........... 260/250 |
| 4,371,720 A | | 2/1983 | Johnson et al. |
| 5,081,122 A | | 1/1992 | Ward |
| 5,292,736 A | | 3/1994 | Kumar et al. |
| 2004/0077650 A1 | | 4/2004 | Dow |

FOREIGN PATENT DOCUMENTS

| DE | 27 36 230 | | 2/1978 |
|---|---|---|---|
| DE | 2736230 | * | 2/1978 |
| EP | 0444451 | | 9/1991 |
| EP | 0570920 | | 11/1993 |
| FR | 2735774 | | 6/1995 |
| JP | 61056230 | * | 12/1986 |
| JP | WO 02/088084 | | 11/2002 |
| WO | WO 94/12466 | | 6/1994 |
| WO | WO 97/29079 | | 8/1997 |
| WO | WO 98/41519 | | 9/1998 |
| WO | WO 99/02499 | | 1/1999 |
| WO | WO 03/07887 | | 1/2003 |
| WO | WO 03/020217 | | 3/2003 |
| WO | WO 03/027069 | | 4/2003 |
| WO | WO 03/027076 | | 4/2003 |
| WO | WO 03/027114 | | 4/2003 |
| WO | WO 03/035005 | | 5/2003 |
| WO | WO 03/051850 | | 6/2003 |
| WO | WO 03/051851 | | 6/2003 |
| WO | WO 03/082191 | | 10/2003 |
| WO | WO 2004/009057 | * | 1/2004 |
| WO | WO 2004/029204 | | 4/2004 |

OTHER PUBLICATIONS

Saikachi et al, Synthesis of furan derivatives. XXXIV. Preparation of 2,3-bis-(5-nitro-2-furyl)pyrazine derivatives, Yakugaku Zasshi, vol. 86(10), 927-932 (1966), as abstracted by Chemical Abstracts Service, from the "CAPLUS" file on STN.*
England and McDougall, "Approaches to Heterocyclic Analogs of Biphenylene. II. 5,5', 6,6'-Tetraphenyl-2,5'-bipyrazinyls" Journal of the Chemical Society; Section C: Organic, vol. 21, pp. 3605-3611 (1971).*
Ohtsuka et al, "Chemistry of Diaminomaleonitrile. 5. Dihydropyrazine Synthesis" Journal of Organic Chemistry, vol. 44(26), pp. 4871-4876 (1979).*
Saikachi et al, Synthesis of furan derivatives. XXXIV. Preparation of 2,3-bis-(5-nitro-2-furyl)pyrazine derivatives, Yakugaku Zasshi, vol. 86(10), 927-932 (1966), English Translation.*
Khuhawar, M.Y., "Infrared studies of pyridyl-substituted pyrazine compounds", Journal of Pure Applied Sciences, vol. 2, No. 1, pp. 9-17, 1983.
Wagner, G. et al., "Uber Die Synthese von O- und S-Glucosiden von Hydroxy-bzw. Mercaptopyrazinen und -chinoxalinen", Zeitschrift für Chemie, vol. 5, No. 3, pp. 104-105, 1965.

* cited by examiner

*Primary Examiner*—Zachary C Tucker
(74) *Attorney, Agent, or Firm*—Maureen S. Gibbons; Burton Rodney

(57) ABSTRACT

The present application describes compounds according to Formula I, wherein A, $G^1$, $G^2$ and $R^1$ are described herein. Additionally, the present application describes pharmaceutical compositions comprising at least one compound according to Formula I and optionally one or more additional therapeutic agents. Finally, the present application describes methods of treatment using the compounds according to Formula I both alone and in combination with one or more additional therapeutic agents

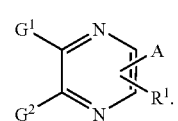

I

7 Claims, No Drawings

PYRAZINE MODULATORS OF CANNABINOID RECEPTORS

RELATED APPLICATIONS

This application claims priority benefit under Title 35 § 119(e) of U.S. Provisional Application No. 60/495,807, filed Aug. 15, 2003, the contents of which are herein incorporated by reference.

BACKGROUND OF THE INVENTION

Delta-9-tetrahydrocannabinol or Delta-9 THC, the principle active component of *Cannabis sativa* (marijuana), is a member of a large family of lipophilic compounds (i.e., cannabinoids) that mediate physiological and psychotropic effects including regulation of appetite, immunosuppression, analgesia, inflammation, emesis, anti-nocioception, sedation, and intraocular pressure. Other members of the cannabinoid family include the endogenous (arachidonic acid-derived) ligands, anandamide, 2-arachidonyl glycerol, and 2-arachidonyl glycerol ether. Cannabinoids work through selective binding to and activation of G-protein coupled cannabinoid receptors. Two types of cannabinoid receptors have been cloned including CB-1 (L. A. Matsuda, et al., *Nature*, 346, 561-564 (1990)), and CB-2 (S. Munro, et al., *Nature*, 365, 61-65 (1993)). The CB-1 receptor is highly expressed in the central and peripheral nervous systems (M. Glass, et al., *Neuroscience*, 77, 299-318 (1997)), while the CB-2 receptor is highly expressed in immune tissue, particularly in spleen and tonsils. The CB-2 receptor is also expressed on other immune system cells, such as lymphoid cells (S. Galiegue, et al., *Eur J Biochem*, 232, 54-61 (1995)). Agonist activation of cannabinoid receptors results in inhibition of cAMP accumulation, stimulation of MAP kinase activity, and closure of calcium channels.

There exists substantial evidence that cannabinoids regulate appetitive behavior. Stimulation of CB-1 activity by anandamide or Delta-9 THC results in increased food intake and weight gain in multiple species including humans (Williams and Kirkham, *Psychopharm.*, 143, 315-317 (1999)). Genetic knock-out of CB-1 result in mice that were hypophagic and lean relative to wild-type litter mates (DiMarzo, et al., *Nature*, 410, 822-825 (2001)). Published studies with CB-1 small molecule antagonists have demonstrated decreased food intake and body weight in rats (Trillou, et. al., *Am. J. Physiol. Regul. Integr. Comp. Physiol.*, R345-R353, (2003)). Chronic administration of the CB-1 antagonist AM-251 for two weeks resulted in substantial body weight reduction and decreased adipose tissue mass (Hildebrandt, et. al., *Eur. J. Pharm*, 462, 125-132 (2003)). There are multiple studies that have assessed the anorexic effect of the Sanofi CB-1 antagonist, SR-141716 (Rowland, et. al., *Pyschopharm.*, 159, 111-116 (2001); Colombo, et. al., *Life Sci.*, 63, 113-117 (1998)). There are at least two CB-1 antagonists in clinical trials for regulation of appetite, Sanofi's SR-141716 and Solvay's SLV-319. Published Phase IIb data reveal that SR-141716 dose-dependently reduced body weight in human subjects over a 16 week trial period. CB-1 antagonists have also been shown to promote cessation of smoking behavior. Phase II clinical data on smoking cessation were presented in September of 2002 at Sanofi-Synthelabo's Information meeting. This data showed that 30.2% of patients treated with the highest dose of SR-141716 stayed abstinent from cigarette smoke relative to 14.8% for placebo.

DETAILED DESCRIPTION OF THE INVENTION

The present application describes compounds according to Formula I, pharmaceutical compositions comprising at least one compound according to Formula I and optionally one or more additional therapeutic agents and methods of treatment using the compounds according to Formula I both alone and in combination with one or more additional therapeutic agents.

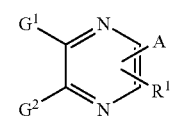

I including all pharmaceutically acceptable salts and stereoisomers, wherein A, $G^1$, $G^2$ and $R^1$ are described herein.

Definitions

The following definitions apply to the terms as used throughout this specification, unless otherwise limited in specific instances.

Unless otherwise indicated, the term "alkyl" as employed herein alone or as part of another group includes both straight and branched chain hydrocarbons, containing 1 to 40 carbons, preferably 1 to 20 carbons, more preferably 1 to 8 carbons, in the normal chain, such as methyl, ethyl, propyl, isopropyl, butyl, sec-butyl, tert-butyl, iso-butyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Further, alkyl groups, as defined herein, may optionally be substituted on any available carbon atom with one or more functional groups commonly attached to such chains, such as, but not limited to alkyl, aryl, alkenyl, alkynyl, hydroxyl, arylalkyl, cycloalkyl, cycloalkylalkyl, alkoxyl, arylalkyloxy, heteroaryloxy, heteroarylalkyloxy, heterocyclyl, alkanoyl, halo, haloalkyl, thio, alkylthio, nitro, cyano, carboxyl, carbonyl, carbalkoyl, carboxamido, amino, alkylamino, dialkylamino, amido, alkylamino, arylamido, heterarylamido, azido, guanidino, amidino, phosphonic, phosphinic, sulfonic, sulfonamido, haloaryl, $CF_3$, $OCF_2$, $OCF_3$, aryloxy, heteroaryl, cycloalkylalkoxyalkyl, cyclohetroalkyl and the like to form alkyl groups such as trifluoro methyl, 3-hydroxyhexyl, 2-carboxypropyl, 2-fluoroethyl, carboxymethyl, cyanobutyl and the like.

Unless otherwise indicated, the term "alkenyl" as employed herein alone or as part of another group includes both straight and branched chain hydrocarbons, containing 2 to 40 carbons with one or more double bonds, preferably 2 to 20 carbons with one to three double bonds, more preferably 2 to 8 carbons with one to two double bonds, in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. Further, alkenyl groups, as defined herein, may optionally be substituted on any available carbon atom with one or more functional groups commonly attached to such chains, such as, but not limited to halo, haloalkyl, alkyl, alkoxy, alkynyl, aryl, arylalkyl, cycloalkyl, amino, hydroxyl, heteroaryl, cyclohetroalkyl, alkanoylamino, alkylamido, arylcarbonylamino, nitro, cyano, thiol, alkylthio and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons with one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like. Further, alkynyl groups, as defined herein, may optionally be substituted on any available carbon atom with one or more functional groups commonly attached to such chains, such as, but not limited to halo, haloalkyl, alkyl, alkoxy, alkenyl, aryl, arylalkyl, cycloalkyl, amino, hydroxyl, heteroaryl, cycloheteroalkyl, alkanoylamino, alkylamido, arylcarbonylamino, nitro, cyano, thiol, alkylthio and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, appended or fused, including monocyclic alkyl, bicyclic alkyl and tricyclic alkyl, containing a total of 3 to 20 carbons forming the rings, preferably 4 to 7 carbons, forming each ring; which may be fused to 1 aromatic ring as described for aryl, which include cyclopropyl, cyclobutyl, cyclopentyl, cyclohexyl, cycloheptyl, cyclooctyl, cyclodecyl, cyclododecyl, cyclohexenyl,

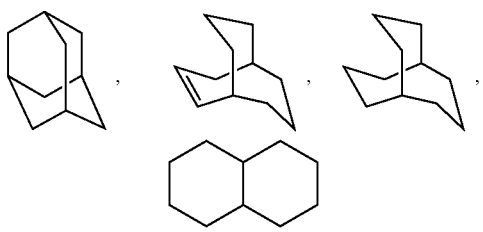

any of which groups may be optionally substituted through any available carbon atoms with 1 or more groups selected from hydrogen, halo, haloalkyl, alkyl, haloalkyl, alkoxy, haloalkoxy, alkenyl, trifluoromethyl, trifluoromethoxy, alkynyl, cycloalkylalkyl, fluorenyl, heterocycloalkyl, heterocycloalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, oxo, cyano, carboxyl, carbonyl, carboxamido, amino, substituted amino wherein the amino includes 1 or 2 substituents (which are alkyl, aryl or any of the other aryl compounds mentioned in the definitions), amido, azido, guanidino, amidino, phosphonic, phosphinic, sulfonic, sulfonamido, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or any of alkyl substituents as set out above.

The term "iminoalkyl" as used herein alone or as part of another group refers to a nitrogen that is doubly-bonded to a carbon wherein said carbon is part of an alkyl group as defined above.

The term "cycloalkylalkyl" as used herein alone or as part of another group refers to alkyl groups as defined above having a cycloalkyl substituent, wherein said "cycloalkyl" and/or "alkyl" groups may optionally be substituted as defined above.

The term "aryl" as employed herein alone or as part of another group refers to monocyclic and bicyclic aromatic groups containing 6 to 10 carbons in the ring portion (such as phenyl or naphthyl) and may optionally include one to three additional rings fused to "aryl", such as aryl, cycloalkyl, heteroaryl, heterocycloalkyl rings,

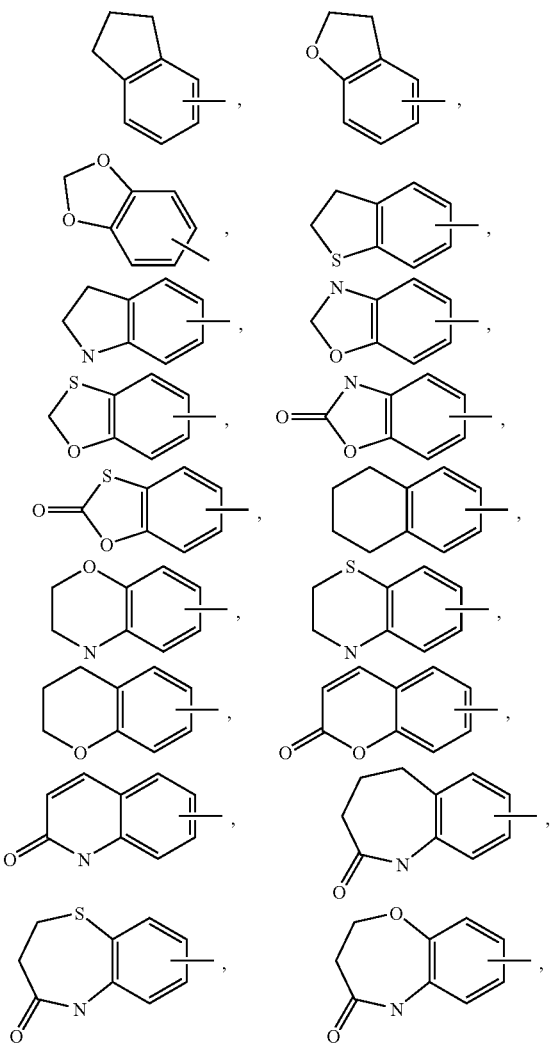

for example. Further, "aryl", as described herein, may optionally be substituted through any available carbon atoms with 1 or more groups selected from hydrogen, alkyl, halo, haloalkyl, alkoxy, haloalkoxy, alkenyl, trifluoromethyl, trifluoromethoxy, alkynyl, cycloalkylalkyl, fluorenyl, heterocycloalkyl, heterocycloalkylalkyl, aryl, heteroaryl, arylalkyl, aryloxy, aryloxyalkyl, arylalkoxy, arylthio, arylazo, heteroarylalkyl, heteroarylalkenyl, heteroaryloxy, hetroarylalkyloxy, hetroarylalkyloxyalkyl, hydroxy, nitro, oxo, cyano, amino, substituted amino wherein the amino includes 1 or 2 substituents (which are alkyl, cycloalkyl, heterocycloalkyl, heteroaryl, or aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, cycloalyklaminocarbonyl, arylaminocarbonyl, heteroarylaminocarbonyl, heteroarylalkylaminocarbonyl alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or any of alkyl substituents as set out above.

The term "arylalkyl" as used herein alone or as part of another group refers to alkyl groups as defined above having an aryl substituent, such as benzyl, phenethyl or naphthylpropyl, wherein said aryl and/or alkyl groups may optionally be substituted as defined above.

The term "alkoxy", "aryloxy", "heteroaryloxy" "arylalkyloxy", or "heteroarylalkyloxy" as employed herein alone or as part of another group includes an alkyl or aryl group as defined above linked through an oxygen atom.

The term "heterocyclo", "heterocycle" "heterocyclyl" or "heterocyclic", as used herein, represents an unsubstituted or substituted stable 4-, 5-, 6- or 7-membered monocyclic ring system which may be saturated or unsaturated, and which consists of carbon atoms and from one to four heteroatoms selected from nitrogen, sulfur, oxygen and/or a SO or $SO_2$ group, wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, oxadiazolyl, tetrahydrofuranyl, tetrahydrothiophenyl, oxadiazolyl,

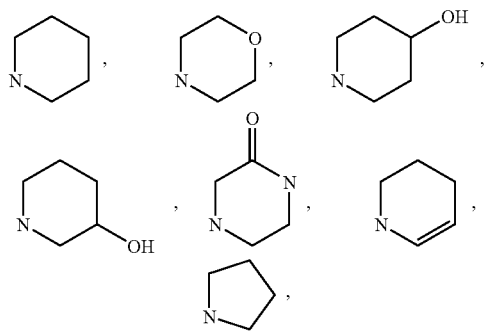

and other heterocycles described in Katritzky, A. R. and Rees, C. W., eds. *Comprehensive Heterocyclic Chemistry: The Structure, Reactions, Synthesis and Uses of Heterocyclic Compounds* 1984, Pergamon Press, New York, N.Y.; and Katritzky, A. R., Rees, C. W., Scriven, E. F., eds. *Comprehensive Heterocyclic Chemistry II: A Review of the Literature* 1982-1995 1996, Elsevier Science, Inc., Tarrytown, N.Y.; and references therein. Optionally a heterocyclo group may be substituted with one or more functional groups, such as those described for "alkyl", "aryl" or "heteroaryl".

The term "heterocycloalkyl" as used herein alone or as part of another group refers to alkyl groups as defined above having a heterocycloalkyl substituent, wherein said "heterocyclo" and/or alkyl groups may optionally be substituted as defined above.

The term "heteroaryl" as used herein refers to a 5-, 6- or 7-membered aromatic heterocyclic ring which contains one or more heteroatoms selected from nitrogen, sulfur, oxygen and/or a SO or $SO_2$ group. Such rings may be fused to another aryl or heteroaryl ring and include possible N-oxides; Examples of such heteroaryl groups include, but are not limited to, furan, pyrrole, thiophene, pyridine, isoxazole, oxazole, imidazole,

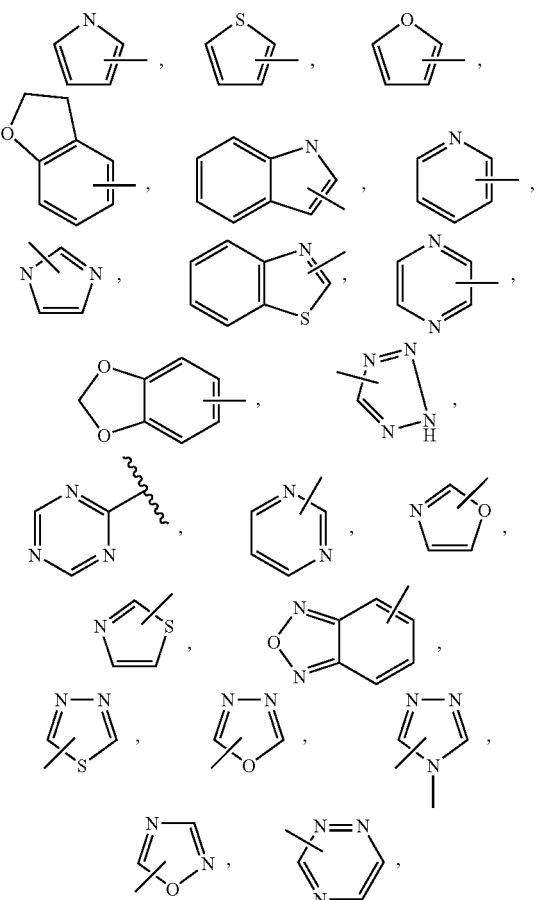

and other heteroaryl groups described in Katritzky, A. R. and Rees, C. W., eds. *Comprehensive Heterocyclic Chemistry: The Structure, Reactions, Synthesis and Uses of Heterocyclic Compounds* 1984, Pergamon Press, New York, N.Y.; and Katritzky, A. R., Rees, C. W., Scriven, E. F., eds. *Comprehensive Heterocyclic Chemistry II. A Review of the Literature* 1982-1995 1996, Elsevier Science, Inc., Tarrytown, N.Y.; and references therein. Optionally a heteroaryl group may be substituted with one or more functional groups commonly attached to such chains, such as those described for "alkyl" or "aryl".

The term "heteroarylalkyl" as used herein alone or as part of another group refers to alkyl groups as defined above having a heteroaryl substituent, wherein said heteroaryl and/or alkyl groups may optionally be substituted as defined above.

Where alkyl groups as defined above have single bonds for attachment to other groups at two different carbon atoms, they are termed "alkylene" groups and may optionally be substituted as defined above for "alkyl".

The term "halogen" or "halo" as used herein alone or as part of another group refers to chlorine, bromine, fluorine, and iodine, with chlorine or fluorine being preferred.

The term "cyano," as used herein, refers to a —CN group.

The term "methylene," as used herein, refers to a —CH$_2$— group.

The term "nitro," as used herein, refers to a —NO$_2$ group.

It is understood that, where necessary, the valency of all atoms is made proper by the addition of hydrogens.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

Analytical HPLC results are reported as retention time in minutes and % homogeneity index (otherwise known as % purity). All analytical HPLC data were recorded on Shimadzu 10A VP HPLC's using monochrome detection at 220 nm. Elution solvent A: 10% MeOH/H$_2$O+0.2% H$_3$PO$_4$; solvent B: 90% MeOH/H$_2$O+0.2% H$_3$PO$_4$. Unless noted, the following conditions apply: column: Phenomenex LUNA C-18 (S5) 4.6×50 mm. Flow rate: 4 mL/min.

$^1$H and $^{13}$C NMR spectra were recorded using Bruker and JEOL spectrometers operating at the following frequencies: $^1$H: 400 MHz and 500 MHz, $^{13}$C: 100 MHz, $^{19}$F: 376 MHz.

Silica ("normal phase") purifications were performed using ISCO combiflash 16×instruments using hexanes and ethyl acetate as the column eluent.

The following abbreviations are employed herein:
Ph=phenyl
Bn=benzyl
t-Bu=tertiary butyl
Me=methyl
Et=ethyl
THF=tetrahydrofuran
Et$_2$O=diethyl ether
EtOAc=ethyl acetate
DMF=dimethyl formamide
MeOH=methanol
EtOH=ethanol
i-PrOH=isopropanol
HOAc or AcOH=acetic acid
TFA=trifluoroacetic acid
i-Pr$_2$NEt=diisopropylethylamine
Et$_3$N=triethylamine
DMAP=4-dimethylaminopyridine
NaBH$_4$=sodium borohydride
KOH=potassium hydroxide
NaOH=sodium hydroxide
LiOH=lithium hydroxide
K$_2$CO$_3$=potassium carbonate
NaHCO$_3$=sodium bicarbonate
Ph$_3$P=triphenylphosphine
Ar=argon
N$_2$=nitrogen
min=minute(s)
h or hr=hour(s)
L=liter
mL=milliliter
µL=microliter
g=gram(s)
mg=milligram(s)
mol=moles
mmol=millimole(s)
meq=milliequivalent
RT=room temperature
sat or sat'd=saturated
aq.=aqueous
NMR=nuclear magnetic resonance
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.H$_2$O=1-hydroxybenzotriazole hydrate
HOAT=1-Hydroxy-7-azabenzotriazole
Pd$_2$(dba)$_3$=tris(dibenzylideneacetone)di-palladium (0)
PPFNMe=(+)-(S)-N,N-dimethyl-1-[(R)-2-(diphenylphosphino)ferrocenyl]methylamine
TLC=thin layer chromatography
HPLC=high performance liquid chromatography
LC/MS=high performance liquid chromatography/mass spectrometry
MS or Mass Spec=mass spectrometry It is anticipated that compounds of formula I can be prepared as prodrugs by one skilled in the art, and the definitions of formula I above include all prodrug, stereoisomers, atropisomers and pharmaceutically acceptable salts of formulas I. Various forms of prodrugs are well known in the art. A comprehensive description of prodrugs and prodrug derivatives are described in:

*The Practice of Medicinal Chemistry*, Camille G. Wermuth et al., Ch 31, (Academic Press, 1996);

*Design of Prodrugs*, edited by H. Bundgaard, (Elsevier, 1985);

*A Textbook of Drug Design and Development*, P. Krogsgaard-Larson and H. Bundgaard, eds. Ch 5, pgs 113-191 (Harwood Academic Publishers, 1991).

Said references are incorporated herein by reference.

Any compound that can be converted in vivo to provide the bioactive agent (i.e., the compound of formula I) is a prodrug within the scope and spirit of the invention.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 8 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C$_1$-C$_4$) alkyl or arylsulfonic acids which are unsubstituted or substituted, for example by halogen, for example methyl- or p-toluene-sulfonic acid.

Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate or nitrate.

Preferred salts of the compounds of formula I which contain an acid group include sodium, potassium and magnesium salts and pharmaceutically acceptable organic amines.

The term "modulator" refers to a chemical compound with capacity to either enhance (e.g., "agonist" activity) or partially enhance (e.g., "partial agonist" activity) or inhibit (e.g., "antagonist" activity or inverse agonist activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The present invention provides for compounds of formula I pharmaceutical compositions employing such compounds and for methods of using such compounds. In particular, the present invention provides for a pharmaceutical composition comprising a therapeutically effective amount of a compound of formula I alone or in combination with a pharmaceutically acceptable carrier.

Further, in accordance with the present invention, a method is provided for preventing, inhibiting or treating the progression or onset of diseases or disorders associated with the cannabinoid receptor, such as the diseases or disorders defined above and hereinafter, wherein a therapeutically effective amount of a compound of formula I is administered to a mammalian, i.e., human patient in need of treatment.

The compounds of the invention can be used alone, in combination with other compounds of the present invention, or in combination with one or more other agent(s) active in the therapeutic areas described herein.

In addition, a method is provided for preventing, inhibiting or treating the diseases as defined above and hereinafter, wherein a therapeutically effective amount of a combination of a compound of formula I and another compound of the invention and/or another type of therapeutic agent, is administered to a mammalian patient in need of treatment.

METHODS OF PREPARATION

The compounds of formula I may be prepared by the exemplary processes described in the following schemes and working examples, as well as relevant published literature procedures that are used by one skilled in the art. Exemplary reagents and procedures for these reactions appear hereinafter and in the working examples. Protection and deprotection in the processes below may be carried out by procedures generally known in the art (see, for example, T. W. Greene & P. G. M. Wuts, "Protecting Groups in Organic Synthesis", 3$^{rd}$ Edition, Wiley, 1999). General methods of organic synthesis and functional group transformations are found in: Trost, B. M. and Fleming, I., eds. *Comprehensive Organic Synthesis: Selectivity, Strategy & Efficiency in Modern Organic Chemistry.* 1991, Pergamon Press, New York, N.Y.; March, J., *Advanced Organic Chemistry: Reactions, Mechanisms, and Structure.* 4th ed. 1992, New York, N.Y.: John Wiley & Sons; Katritzky, A. R., Meth-Cohn, O. and Rees, C. W., eds. *Comprehensive Organic Functional Group Transformations.* 1st ed. 1995, Elsevier Science Inc., Tarrytown, N.Y.; Larock, R. C., *Comprehensive Organic Transformations.* 1989, New York, N.Y.: VCH Publishers, Inc.; and references therein.

Process 1

Compounds of formula I of the invention where A is $NR^2R^3$, $OR^9$, heteroaryl or $CR^4R^5R^6$ may be prepared as depicted by coupling compounds of formula (II) where L is a leaving group such as bromine, chlorine, OTf, with M—A where M is hydrogen or metalloid, such as boron, tin, zinc, copper, potassium, sodium and the like. This coupling may be facilitated by catalysts such as Pd(0), Cu(I) and the like. Examples of these transformations can be found in: Wagaw, S. and Buchwald, S. L., *J. Org. Chem.*, 1996, 61(21), 7240-7241; Konno, S. et al., *Chem. Pharm. Bull.*, 1982, 30(1), 152-157; Abdel-Rahman, R. M. and Ghareib, M., *Indian J. Chem.*, 1987, 26B, 496-500; Saad, H. A. et al., *Indian J. Chem.*, 1998, 37B, 1142-1148; Wolfe, J. P. et al., *Acc. Chem. Res.*, 1998, 31(12), 805-818; Wolfe, J. P. et al., *J. Org. Chem.*, 2000, 65(4), 1158-1174; Hartwig, J. F., *Acc. Chem. Res.*, 1998, 31(12), 852-860; Alonso, D. A. et al., *J. Org. Chem.*, 2002, 67(46), 5588-5594; Miyaura, N. and Suzuki, A., *Chem. Rev.*, 1995, 95(7), 2457-2483; Littke, A. F. et al., *J. Am. Chem. Soc.*, 2000, 122(17), 4020-4028; Nishimura, M. et al., *Tetrahedron*, 2002, 58, 5779-5787; Miller, J. A. and Farrell, R. P., *Tetrahedron Lett.*, 1998, 39(40), 7275-7278; Mitchell, T. N., *Synthesis*, 1992(9), 803-815; Sato, N. and Narita, N., *Synthesis*, 2001(10), 1551-1555; and references therein.

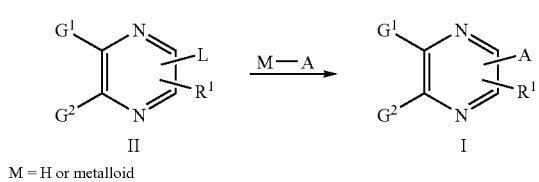

M = H or metalloid

Process 2

Compounds of formula III depicted below are useful intermediates and compounds of this formula may be synthesized by the coupling of cyanide-containing complexes such as CuCN, NaCN and the like to compounds of formula II as described in process 1. Examples of this transformation are found in: Karmas, G. and Spoerri, P. E., *J. Am. Chem. Soc.*, 1956, 78(10), 2141-2144; Matsuda, T. et al. *Bioorg. Med. Chem. Lett.*, 2001(11), 2369-2372; Konno, S. et al., *Chem. Pharm. Bull.*, 1982, 30(1), 152-157; Akita, Y., Shimazaki, M. and Ohta, A., *Synthesis*, 1981(12), 974-975; and references therein.

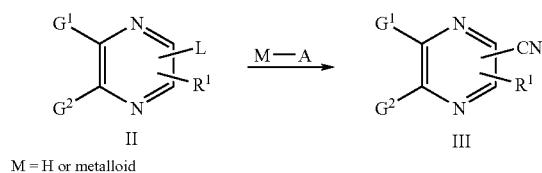

M = H or metalloid

Process 3

Intermediates of formula III are useful for the synthesis of compounds of formula I where A is optionally substituted heteroaryl, C(O)NR²R³ and CR⁴R⁵R⁶ as depicted below and as described, for example, in: Moody, C. J., ed. *Synthesis: Carbon with Two Attached Heteroatoms with at Least One Carbon-to-heteroatom Multiple Link.* Comprehensive Organic Functional Group Transformations, ed. A. R. Katritzky, O. Meth-Cohn, and C. W. Rees. Vol. 5. 1995, Elsevier Science Inc., Tarrytown, N.Y. 1308; March, J., *Advanced Organic Chemistry: Reactions, Mechanisms, and Structure.* 4th ed. 1992, New York, N.Y.: John Wiley & Sons; Harrison, I. T. and Harrison, S., *Compendium of Organic Synthetic Methods.* 1971, New York, N.Y.: Wiley-Interscience; Katritzky, A. R., Meth-Cohn, O. and Rees, C. W., eds. *Comprehensive Organic Functional Group Transformations.* 1st ed. 1995, Elsevier Science Inc., Tarrytown, N.Y.; and references therein.

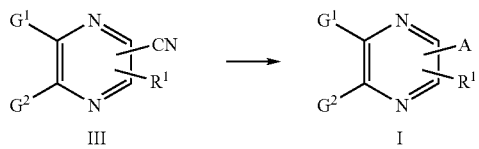

Process 4

Compounds of formula I where A is selected from the group including NR²R³, OR⁹, SR⁷, S(O)R⁸, S(O)₂R⁸, CR⁴R⁵R⁶ may be prepared as depicted by coupling compounds of formula II where L is a leaving group such as Cl, Br, OTf and the like with A—H, or a precursor of A known to those skilled in the art, directly—or in the presence of a base such as TEA, pyridine, KOH, K₂CO₃, NaH or the like as exemplified herein and described, for example, in: Nannini, G. et al., *Eur. J. Med. Chem.-Chimica Therapeutica*, 1979, 14(1), 53-60; Matsuda, T. et al., *Bioorg. Med. Chem. Lett.*, 2001(11), 2369-2372; Konno, S. et al., *Chem. Pharm. Bull.*, 1982, 30(1), 152-157; Sato, N. and Narita, N., *Synthesis*, 2001(10), 1551-1555; and references therein.

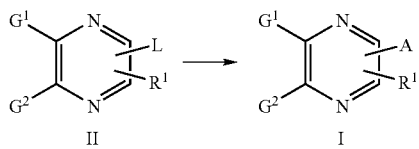

Process 5

A general method for the synthesis of compounds of formula I where A is C(O)NR²R³ is depicted below. A carboxylic acid of formula IV is activated with reagents such as oxalyl chloride, thionyl chloride and the like, then coupled with amines of formula HNR²R³ to give compounds of formula V using conditions exemplified herein or conditions known to those skilled in the art and described, for example, in: Benz, G., *Synthesis of Amides and Related Compounds*, in *Comprehensive Organic Synthesis: Selectivity, Strategy & Efficiency in Modern Organic Chemistry*, B. M. Trost and I. Fleming, Editors. 1991, Pergamon Press: New York, N.Y. p. 381-417, and references therein. Amines of formula HNR²R³ are either commercially available, or can be synthesized according to methods known to those skilled in the art.

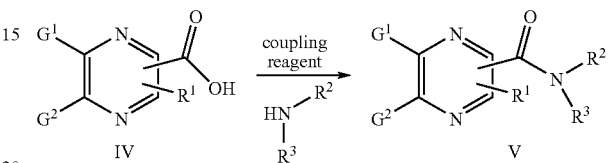

Process 6

Compounds of formula I where A is $S(O)_2R^8$ and $R^8$ is $NR^2R^3$ may be prepared as shown below by coupling compounds of formula II, where L is a leaving group such as Cl, Br, OTf and the like, with sodium sulfite in an appropriate solvent such as water, DMF or the like to give an intermediate compound of formula VI that can be further reacted by methods known to those skilled in the art to give compounds of formula I where A is $SR^7$, $S(O)R^8$ or $S(O)_2R^8$ as exemplified in: Konno, S. et al., *Chem. Pharm. Bull.*, 1982, 30(1), 152-157; and references therein.

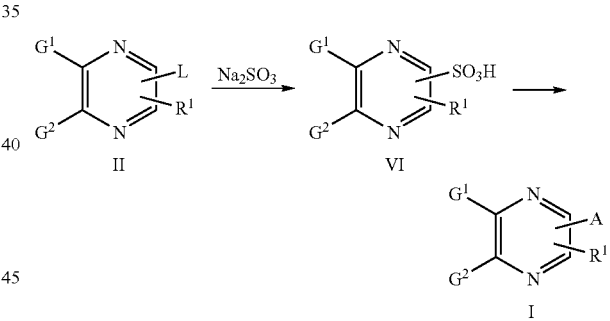

Process 7

Compounds of formula I where A is $SR^7$, $S(O)R^8$ or $S(O)_2R^8$ may be prepared as shown below from compounds of formula II where L is a halogen such as Cl, Br, I and the like by exchange with a metalloid compound such as n-butyllithium, isopropylmagnesium chloride, lithium napthalide and the like as described, for example, in: Mongin, F. and Queguiner, G. *Tetrahedron*, 2001, 57(19), 4059-4090; Turck, A. et al. *Tetrahedron*, 2001, 57(21), 4489-4505; to give a compound of formula VIII where J is a metalloid such as lithium or magnesium and the like, or such metal is exchanged for another metal such as zinc, tin, palladium and the like. Compounds of formula VIII can be reacted with sulfur electrophiles such as $R^7SSR^7$ or $SO_2Cl_2$ as described, for example, in Hamada, T. and Yonemitsu, O. *Synthesis*, 1986, 852-854; to give intermediates that can be converted to compounds of formula (I) by methods known to those skilled in the art.

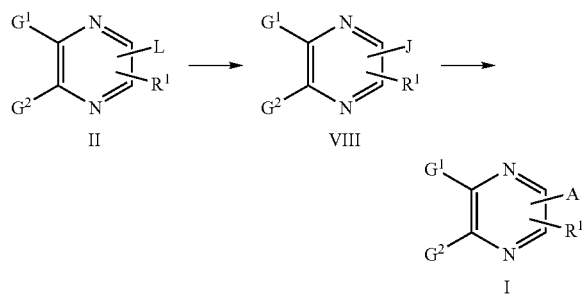

Process 8

Compounds of formula I where A is $S(O)R^8$ may be prepared by coupling compounds of formula II, where L is a leaving group such as Cl, Br, OTf and the like, with a sulfur nucleophile such as $Na_2S$, NaSAc and the like to give, upon further functionalization according to methods known to those skilled in the art, a compound of formula I where A is $SR^7$, $S(O)R^8$ or $S(O)_2R^8$.

Process 9

A general sythetic approach to intermediates of formula II is depicted below. In the general process, intermediate IX may be activated to form a leaving group (L) such as Cl, Br, OTf and the like, using activating reagents such as $POCl_3$, $POBr_3$, $Tf_2O$ and the like. Compounds of formula II are useful intermediates, as described in process 1, 2, 4, 6, 7, and 8 above. Examples of these transformations and the synthesis of compounds of formula IX are exemplified herein and can be found in: Konno, S. et al., *Chem. Pharm. Bull.*, 1982, 30(1), 152-157; Karmas, G. and Spoerri, P. E., *J. Am. Chem. Soc.*, 1952, 74, 1580-1584; Nannini, G. et al., *Eur. J. Med. Chem.-Chimica Therapeutica*, 1979, 14(1), 53-60; Matsuda, T. et al., *Bioorg. Med. Chem. Lett.*, 2001(11), 2369-2372; Wagaw, S. and Buchwald, S. L., *J. Org. Chem.*, 1996, 61(21), 7240-7241; Culkin, D. A. and Hartwig, J. F., *Acc. Chem. Res.*, 2003, 36(4), 234-245; Hartwig, J. F., *Acc. Chem. Res.*, 1998, 31(12), 852-860; Wolfe, J. P. et al., *Acc. Chem. Res.*, 1998, 31(12), 805-818; and references therein.

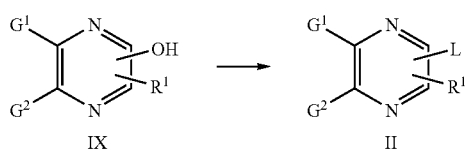

Process 10

Compounds of formula IX may be synthesized by the method of Karmas, G. and Spoerri, P. E., *J. Am. Chem. Soc.*, 1952, 74, 1580-1584; and, Jones, R., *J. Am. Chem. Soc.*, 1949, 71, 78-81, involving the condensation of an appropriately substituted diketone X to the appropriate amine-containing compound XI to provide intermediate IX as depicted below. Intermediate IX may be further elaborated by methods know to those skilled in the art to generate compounds of formula I where A is $OR^9$ or intermediates of formula II as described in process 9.

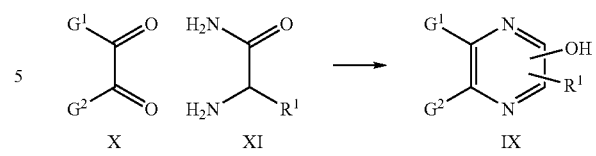

Process 11

The synthesis of diketone intermediates of formula X is depicted below and is described in March, J., *Advanced Organic Chemistry: Reactions, Mechanisms, and Structure.* 4th ed. 1992, New York, N.Y.: John Wiley & Sons; Matsumoto, T. et al., *J. Org. Chem.*, 1985, 50(5), 603-606; Miyashita, A. et al., *Chem. Pharm. Bull.*, 1994, 42(12), 2633-2635; and references therein, wherein two aldehydes are coupled to form a di-oxygenated intermediate XII that can be oxidized, if necessary, to form the desired aryl diketone. Alternatively, activated aryl moieties can be added sequentially to a 1,2-dicarbonylcompound where Z is a leaving group such as —N(OMe)Me and the like to give symmetrical and un-symmetrical benzils intermediate XIII as described in Mueller-Westerhoff, U. T. and Zhou, M., *J. Org. Chem.*, 1994, 59(17), 4988-4992, and Sibi, M. P. et al., *J. Org. Chem.*, 1995, 60(16), 5016-5023. Other methods for synthesizing 1,2-dicarbonyl compounds can be found, for example, in McKenna, J. M. et al., *J. Med. Chem.*, 2002, 45(11), 2173-2184; Walsh, C. J. and Mandal, B. K., *J. Org. Chem.*, 1999, 64(16), 6102-6105; and references therein.

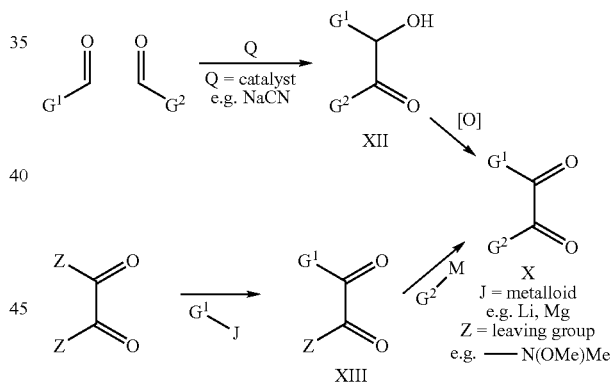

Process 12

A general method for the synthesis of compounds of formula I where A is $C(O)NR^2R^3$ and $R^1$ is H is depicted below. A dicarbonyl compound of formula X is condensed with a diamino-compound of formula XIV in a solvent such as methanol or glacial acetic acid at an elevated temperature exposed to atmosphere to give compounds of formula XV.

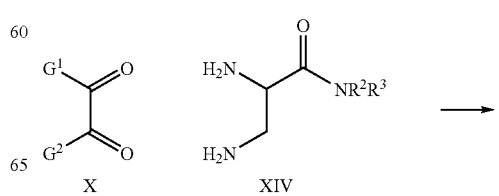

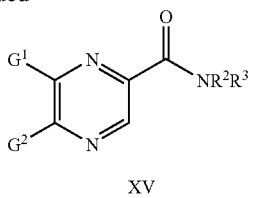

XV

Process 13

An alternative general method for the synthesis of compounds of formula I where A is C(O)NR²R³ is depicted where a dicarbonyl compound of formula X is condensed with methyl 2,3-diaminopropionate XVI in a solvent, such as methanol or glacial acetic acid, at an elevated temperature exposed to atmosphere. The resultant intermediate XVII is deprotected to form carboxylic acid-containing intermediate XVIII that is coupled with amines via conditions that are known to those skilled in the art to give compounds of formula XV.

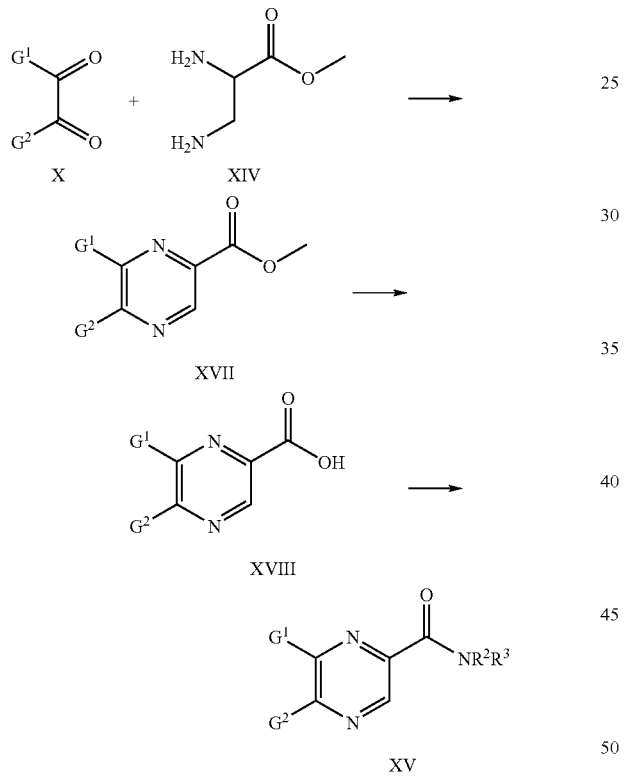

Where they are not commercially available, the starting materials of formula II-XVIII may be prepared by methods analogous to those described in the general processes or accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I wherein A represents COOH initially obtained may be activated with oxalyl chloride, thionyl chloride and the like, or a carbodiimide such as di-isopropylcarbodiimide, di-cyclohexylcarbodiimide and the like followed by reaction with an amine containing compound of formula HNR²R³ to form the corresponding compound of formula I wherein A is C(O)NR²R³.

EXAMPLES

The following examples serve to better illustrate, but not limit, some of the preferred embodiments of the invention.

Example 1

5,6-Bis-(4-methylphenyl)-2-(2-(2S)-(4-methyl-1-hydroxypentyl)aminocarbonyl)pyrazine

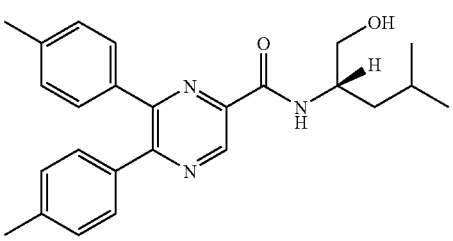

Example 1A

Methyl 2,3-diaminopropionate bis-hydrochloride salt

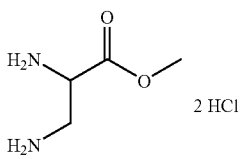

Following the procedure of Jones, P. et al., *J. Med. Chem.*, 1998, 41 (16), 3062-3077, 2,3-diaminopropionic acid (1.77 g, 12.6 mmol) was suspended in 40 mL of MeOH at 0° C. and HCl gas was bubbled through the solution until homogeneous. The reaction solution was warmed to 60° C. for 12 h and evaporated to dryness to give 2.4 g (100%) of example 1A methyl 2,3-diaminopropionate bis-hydrochloride. This material was used without further purification.

¹H NMR (D₂O, 400 MHz) δ 4.49 (dd, 1H, J=5.2, 8.1 Hz), 3.85 (s, 3H), 3.58 (dd, 1H, J=8.1, 13.8 Hz), 3.49 (dd, 1H, J=5.4, 13.8 Hz)

Example 1B

Methyl 5,6-bis-(4-methylphenyl)pyrazin-2-carboxylate

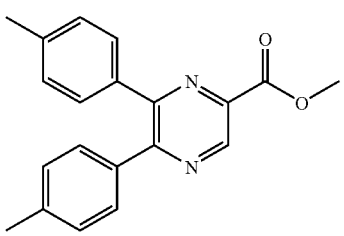

Methyl 2,3-diaminopropionate example 1A (2.4 g, 12.6 mmol) was shaken vigorously for 5 min in a solution of KOH (2.1 g, 37.7 mmol) in 20 mL of MeOH. The resulting milky solution was filtered to remove the solids, and the filtrate was added to a solution of 4,4'-dimethylbenzil (4.48 g, 18.8 mmol) in 20 mL of MeOH. The resulting mixture was heated to 65° C. for 14 h with a reflux condenser open to air. Solvent was evaporated and the residue was dissolved in 300 mL of EtOAc and 200 mL of 1N HCl. The layers were extracted and the organic layer was evaporated to give a thick oil that was redissolved in 5 mL of $CH_2Cl_2$ and this solution was loaded onto dry 120 g silica cartridge. The solvent was evaporated with a stream of $N_2$, and the desired product example 1B was eluted with a gradient of 0-40% EtOAc/hexanes to give 1.71 g of a yellow solid.

$^1$H NMR ($CDCl_3$, 400 MHz) δ 9.25 (s, 1H), 7.42 (d, 4H, J=7.8 Hz), 7.14 (d, 4H, J=7.8 Hz), 4.05 (s, 3H), 2.38 (s, 3H), 2.37 (s, 3H).

$^{13}$C NMR ($CDCl_3$, 100 MHz) δ 165.3, 155.7, 143.1, 140.3, 139.9, 139.4, 135.5, 130.1, 130.0, 129.9, 129.5, 129.4, 53.2, 21.7, 21.6.

Example 1C 5,6-Bis-(4-methylphenyl)pyrazin-2-carboxylic acid

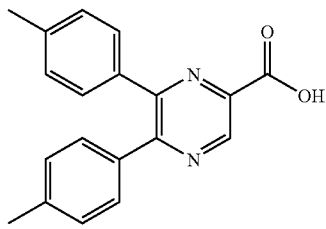

Intermediate 1B (1.3 g, 4.1 mmol) was dissolved in 20 mL of DMF and 10 mL of $H_2O$. LiOH (0.5 g, 12 mmol) was added, and the solution was stirred for 3 h. The reaction solution was diluted with 300 mL of EtOAc and 400 mL of 0.1 N aq. NaOH. The layers were extracted and the aqueous layer was acidified (conc. HCl) to pH 1 to give a cloudy solution that was extracted with 400 mL of EtOAc. The organic layer was washed with 400 mL of 0.2 N aq. HCl then 400 mL of brine. The organic layer was dried over $MgSO_4$, filtered and evaporated to give 1.1 g (89%) of example 1C as a yellow solid. This material was used without further purification.

Example 1D 5,6-Bis-(4-methylphenyl)-2-(2-(2S)-(4-methyl-1-hydroxypentyl)aminocarbonyl)pyrazine

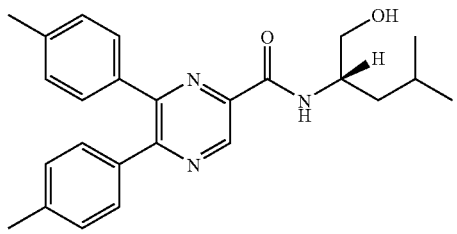

Example 1C (0.8 g, 2.6 mmol) was dissolved in 26 mL of $CH_2Cl_2$ and 0.1 mL of DMF at 0° C. and oxalyl chloride was added (9.2 mL of 2M oxalyl chloride in $CH_2Cl_2$, 18 mmol). The reaction solution was stirred for 10 min at 0° C. and was stirred at RT for 2 h. The solution was evaporated in vacuo to give a yellow solid that was redissolved in 10 mL of $CH_2Cl_2$ at 0° C. To the resulting solution was added S-(+)-leucinol (1 mL, 8 mmol) and triethylamine (1.1 mL, 10 mmol). The reaction solution was stirred for 10 min at 0° C. and for 2 h at RT. The crude reaction mixture was loaded onto a dry 40 g silica cartridge and the solvent was evaporated with a stream of nitrogen. The desired product was eluted using a gradient from 0-60% EtOAc/hexanes over 50 min to give 0.55 g (52%) of example 1 as a white solid.

HPLC: 4.15 min retention time, 95.7% homogeneity index; Column: Phenomenex LUNA S-5 C18 4.6×50 mm. Gradient: 0-100% B over 4 min, hold at 100% B for 1 min. Solvent A: 10% MeOH/$H_2O$+0.2% $H_3PO_4$. Solvent B: 90% MeOH/$H_2O$+0.2% $H_3PO_4$.

$^1$H NMR ($CDCl_3$, 400 MHz) δ 9.27 (s, 1H), 7.83 (d, 1H, J=8.2 Hz), 7.30 (dd, 4H, J=5.0, 3.2 Hz), 7.07 (dd, 4H, J=7.9, 9.6 Hz), 4.25-4.17 (m, 1H), 3.74 (dd, 1H, J=3.6, 11.1 Hz), 3.60 (dd, 1H, J=6.0, 11.1 Hz), 3.44 (br s, 1H), 2.32 (s, 3H), 2.29 (s, 3H), 1.68-1.38 (m, 3H), 0.90 (d, 6H, J=6.5 Hz).

HRMS calc'd for $C_{25}H_{29}N_3O_2$ m/z 403.22598. Found [M+H] 404.23381.

Example 2

5,6-Bis-(4-methylphenyl)-2-(phenoxyethylaminocarbonyl)pyrazine

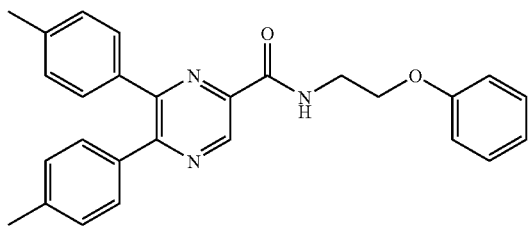

Example 2A (+/−)-N,N'-Bis-(t-butyloxycarbonyl)-2,3-diaminopropionic acid

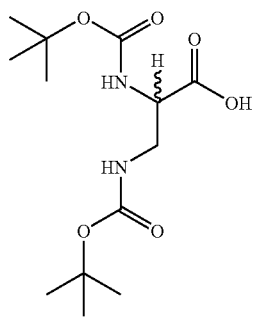

Di-tert-butyl dicarbonate (8.5 g, 39.1 mmol) was added to a solution of D,L-2,3-diaminopropionic acid monohydrochloride salt (2.5 g, 17.8 mmol) in 40 mL of 50% dioxane/water and triethylamine (12.4 mL, 89 mmol). The solution was stirred for 10 h and the mixture was diluted with 200 mL of EtOAc and 50 mL of 1N aq. HCl. The layers were extracted and the organic layer was washed with 50 mL of brine. The organic layer was dried over MgSO₄, filtered and evaporated to give 5.4 g of example 2A isolated as a white solid.

$^1$H NMR (CDCl$_3$, 400 MHz) δ 12.6 (s, 1H), 6.9 (d, 1H, J=7 Hz), 4.0 (dd, 1H, J=7, 6.8 Hz), 3.2 (m, 2H), 1.38 (s, 9H), 1.37 (s, 9H)

Example 2B (+/−)-2',3'-(Diamino)propylcarboxamido-2-phenoxyethane bis-(2,2,2-trifluoroacetic acid) salt

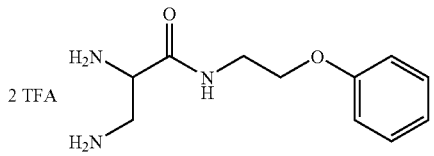

2-Phenoxyethylamine (0.27 g, 2 mmol) was added to a mixture of example 2A (0.5 g, 1.64 mmol), EDC (0.38 g, 1.97 mmol), HOBt (0.3 g, 1.97 mmol), DIEA (0.86 mL, 4.92 mmol) in 16 mL of THF. The mixture was stirred at room temp for 16 h and the volatile components were evaporated in vacuo. The residue was dissolved in 0.5 mL of CH$_2$Cl$_2$ and this solution was loaded onto 40 g silica column, and the solvent was evaporated with a stream of nitrogen. The material was eluted with a gradient of 0-50% EtOAc/hexanes over 20 min to give 0.6 g of a white solid. The solid (0.05 g, 0.13 mmol) was dissolved in 0.6 mL of CH$_2$Cl$_2$ and 0.6 mL of TFA. The solution was stirred for 16 h and the solvents were evaporated to give 0.016 g of example 2B as a yellow oil. The material was used without further purification.

Example 2C 5,6-Bis-(4-methylphenyl)-2-(phenoxyethylaminocarbonyl)pyrazine

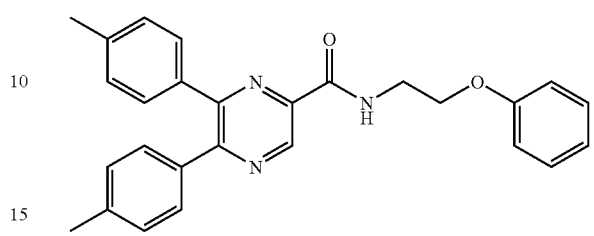

4,4'-dimethylbenzil (0.03 g, 0.12 mmol) and example 2B (0.06 g, 0.11 mmol) were stirred in HOAc (1.2 ml) at 50° C. for 72 h and the solvent was evaporated. The residue was dissolved in 2 mL of 90% MeOH/H$_2$O and the solution was purified via semi-preparative reverse-phase preparative HPLC to give 0.016 g (32%) of example 2 as a brown solid.

Semi-preparative HPLC Conditions
Flow rate: 40 mL/min
Solvent A: 10% CH$_3$CN−90% H2O−0.1% TFA
Solvent B: 90% CH$_3$CN−10% H2O−0.1% TFA
Column: YMC S5 ODS 30×100 mm
Gradient: 30-100% B over 10 min, hold at 100% B for 8 min.
product elutes at: 10.7 min.
Analytical HPLC: 4.43 min retention time, 93.3% homogeneity index.

$^1$H NMR (CDCl$_3$, 400 MHz) δ 9.35 (s, 1H), 8.40 (app t, 1H, J =6.0 Hz), 7.41-6.95 (m, 9H), 4.21 (t, 2H, J=5.2 Hz), 3.95 (q, 2H, J=5.5 Hz), 3.22 (br s, 1H), 2.41 (s, 3H), 2.38 (s, 3H). Anal. Calc'd for C$_{27}$H$_{25}$N$_3$O$_2$ 423.19468. Found HRMS [M+H] 424.2036.

Examples 3-17

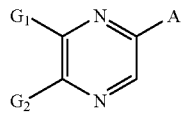

| Example # | name | G1 | G2 | A | HPLC ret. time | [M + H] |
|---|---|---|---|---|---|---|
| 3 | 5,6-Bis-(4-methylphenyl)-2-(2-(2S)-(3-methyl-1-hydroxybutyl)aminocarbonyl)pyrazine | 4-MePh | 4-MePh | (S) isobutyl hydroxymethyl amide | 4.00 | 390.25 |
| 4 | 5,6-Bis-(4-methylphenyl)-2-(2-(2R,S)-(1-hydroxypentyl)aminocarbonyl)pyrazine | 4-MePh | 4-MePh | (S,R) propyl hydroxymethyl amide | 4.04 | 390.26 |

-continued

[Structure: pyrazine core with G1 at position 5, G2 at position 6, and A at position 2]

| Example # | name | G1 | G2 | A | HPLC ret. time | [M + H] |
|---|---|---|---|---|---|---|
| 5 | 5,6-Bis-(4-methyl-phenyl)-2-(2-(2R)-(4-methyl-1-hydroxy-pentyl)aminocarbonyl)pyrazine | 4-MePh | 4-MePh | [(R)-leucinol amide structure] | 4.14 | 404.26 |
| 6 | 5,6-Bis-(4-methyl-phenyl)-2-(2-(2R)-(3-methyl-1-hydroxy-butyl)aminocarbonyl)pyrazine | 4-MePh | 4-MePh | [(R)-valinol amide structure] | 4.00 | 390.24 |
| 7 | 5,6-Bis-(4-methyl-phenyl)-2-(2-hydroxyethylaminocarbonyl)pyrazine | 4-MePh | 4-MePh | [ethanolamine amide structure] | 3.62 | 348.21 |
| 8 | 5,6-Bis-(4-methyl-phenyl)-2-(2-(2S)-(3-methylbutylcarboxamide)aminocarbonyl)pyrazine | 4-MePh | 4-MePh | [(S)-leucinamide structure] | 4.07 | 417.20 |
| 9 | 5,6-Bis-(4-methyl-phenyl)-2-(2-(+/−)-(3-phenylpropion-1-amide)aminocarbonyl)pyrazine | 4-MePh | 4-MePh | [phenylalaninamide structure] | 4.00 | 451.12 |
| 10 | 5,6-Bis-(4-methyl-phenyl)-2-(2-(+/−)-(2-phenylacet-1-amide)aminocarbonyl)pyrazine | 4-MePh | 4-MePh | [phenylglycinamide structure] | 3.97 | 437.10 |
| 11 | 5,6-Bis-(4-methyl-phenyl)-2-((4-phenyl-carbonyl)piperidin-1-yl-carbonyl)pyrazine | 4-MePh | 4-MePh | [4-benzoylpiperidine amide structure] | 1.68 | 476.39 |

-continued

| Example # | name | G1 | G2 | A | HPLC ret. time | [M + H] |
|---|---|---|---|---|---|---|
| 12 | 5,6-Bis-(4-methyl-phenyl)-2-(1-(2,6-dimethylphenoxy)propyl-2-aminocarbonyl)pyrazine | 4-MePh | 4-MePh | | 2.10 | 466.25 |
| 13 | 5,6-Bis-(4-methyl-phenyl)-2-(2-biphenyl)methylaminocarbonyl)pyrazine | 4-MePh | 4-MePh | | 2.17 | 470.23 |
| 14 | 5,6-Bis-(4-methyl-phenyl)-2-(1-benzyloxybutyl-2-(2R)-aminocarbonyl)pyrazine | 4-MePh | 4-MePh | | 2.09 | 466.25 |
| 15 | 1,4-Bis-(5,6-bis-(4-methylphenyl)pyrazinylcarbonyl)piperazine | 4-MePh | 4-MePh | | 4.69 | 659.46 |
| 16 | N,N'-Bis-(5,6-bis-(4-methylphenyl)pyrazinylcarbonyl)piperazinylmethylamine | 4-MePh | 4-MePh | | 4.76 | 687.34 |
| 17 | 5,6-Bis-(4-chlorophenyl)-2-(2-(2S)-(4-methyl-1-hydroxypentyl)aminocarbonyl)pyrazine | 4-Cl | 4-Cl | | 4.23 | 444.21 |

Example 17A 5,6-Bis-(4-chlorophenyl)-2-(2-(2S)-(4-methyl-1-phosphoryloxypentyl)aminocarbonyl)pyrazine

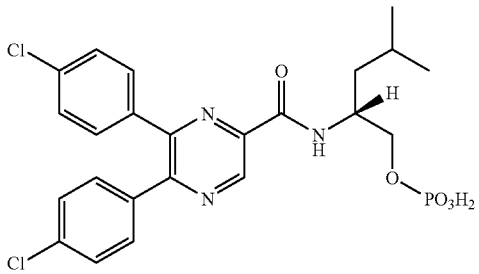

Example 17A was envisioned as a pro-drug utilizing the hydroxyl group of example 17 and as such was not submitted for biological testing A solution of POCl$_3$ (0.008 mL, 0.084 mmol). in 0.2 mL of THF was stirred at 0° C. for 30 min and a solution of pyridine (0.022 mL, 0.28 mmol) in 0.2 mL of THF was added. To the reaction solution was added 25 mg of example 8 (0.056 mmol) in 0.2 mL of THF. The resultant mixture was stirred at 0° C. for 1 h and at room temperature for 15 h. Hydrolysis of the chlorophosphate was performed upon quench with ice water. The mixture was stirred vigorously for 1 h and the pH was adjusted with 1N HCl to pH 1 before extraction with 5 mL of EtOAc. The layers were separated and the organic layer was washed with brine and evaporated to give a residue that was purified via preparative reverse-phase HPLC to give 0.002 g of example 17A as a beige solid.

Analytical HPLC: 4.54 min retention time, >99% homogeneity index.

$^1$H NMR (CD$_3$CN+drop of D$_2$O, 400 MHz) δ 9.2 (s, 1H), 7.45-7.2 (m, 8H), 4.3 (br s, 1H), 4.0-3.8 (m, 2H), 1.6-1.5 (m, 2H), 1.4-1.3 (m, 1H), 0.86 (d, 6H, J=8 Hz) LCMS: Anal. Calcd. for C$_{23}$H$_{24}$Cl$_2$N$_3$O$_5$P 523.08. Found: 524.27 [M+H].

Example 18

5,6-Bis(4-methylphenyl)-2-piperidinylpyrazine

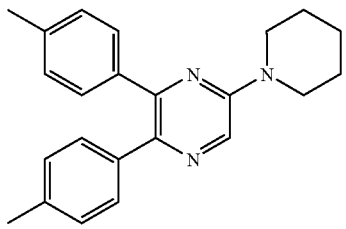

Example 18A

2-Chloro-5,6-bis-(4-methylphenyl)pyrazine

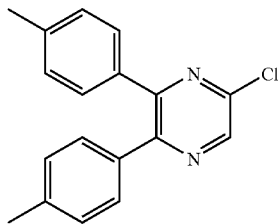

A suspension of glycinamide (0.4 g, 3.6 mmol) and 4,4'-dimethylbenzil (1.03 g, 4.3 mmol) in 7.7 mL of 10% aq. MeOH was cooled to −40° C. and a solution of NaOH (0.36 g in 0.7 mL of H$_2$O) was added portionwise over 5 min. The solution was stirred vigorously at −40° C. for 30 min and 24 h at RT. The reaction was quenched with 0.36 mL of 12 N HCl and the solution was evaporated to dryness to give 1 g of yellow solid. The solids were dissolved in 6 mL of POCl$_3$ and conc. H$_2$SO$_4$ (~0.5 mL) was added until the solution turned to a homogeneous dark red solution. After heating to 105° C. for 16 h, the cooled (RT) solution was poured over 300 mL of ice. The resulting slurry was diluted with 300 mL of ether and the layers were extracted. The aqueous layer was extracted with 200 mL of ether, and the combined organic layers were washed with 300 mL of water then 300 mL of brine. The organic layer was dried over MgSO$_4$, filtered, and evaporated to give a yellow solid that was dissolved in 3 mL of CH$_2$Cl$_2$. The solution was loaded onto dry 120 g silica cartridge and the solvent was evaporated with a stream of nitrogen. The product was eluted with a gradient of 0-25% EtOAc/hexanes to give 1.06 g (99%) of example 18A as a yellow solid.

Example 18B 5,6-Bis(4-methylphenyl)-2-piperidinylpyrazine

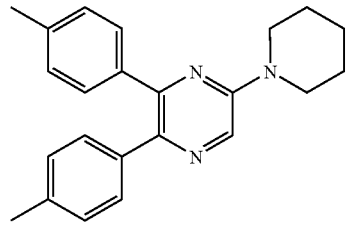

A solution of example 18A (0.05 g, 0.17 mmol) in 0.25 mL of piperidine was stirred for 16 h at room temp then heated to 65° C. for 6 h. The solution was cooled to room temp and was stirred for 3 d. The reaction solution was evaporated to dryness then redissolved in 4 mL of 90% MeOH/H$_2$O. The product was purified via semi-preparative reverse-phase HPLC to give 0.01 g of example 18-TFA salt as a yellow solid.

Preparative HPLC Conditions column: YMC S5 ODS (C-18) 30×250 mm gradient: 20-100% B over 30 min, hold at 100% B for 20 min.

Solvent A: 10% MeOH/H$_2$O+0.1% TFA

Solvent B: 90% MeOH/H$_2$O+0.1% TFA

Flow rate: 20 mL/min

Monochrome detection at 220 nm.

Product elutes at 45.4 min.

Product analytical HPLC: 4.49 min retention time, 95.0% homogeneity index.

$^1$H NMR (CD$_3$OD, 400 MHz) δ 7.98 (s, 1H), 7.16-6.95 (m, 8H), 3.62-3.59 (m, 4H), 2.21 (s, 6H), 1.61-1.58 (m, 6H).

$^{19}$F NMR (CD$_3$OD, 376 MHz) δ −77.09 ppm. HRMS: Anal. Calcd. for C$_{23}$H$_{25}$N$_3$ 343.20485. Found: 344.2127 [M+H]

Example 19

5,6-Bis(4-methylphenyl)-2-(4-isopropylpiperazinyl)pyrazine

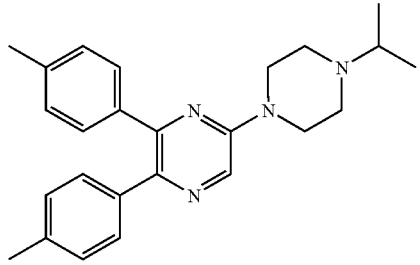

Synthesized according to the method of example 18 to give 8 mg of example 19 as a yellow foam. Product analytical HPLC: 2.87 min retention time, 88.4% homogeneity index.

$^1$H NMR (CDCl$_3$, 500 MHz) δ 8.31 (s, 1H), 7.28-7.1 (m, 8H), 4.61 (d, 2H, J=12.7 Hz), 3.68-3.63 (m, 5H), 3.05-2.95 (m, 2H), 2.35 (s, 6H), 1.40 (d, 6H, J=6.0 Hz). LCMS: Anal. Calcd. for C$_{25}$H$_{30}$N$_4$ 386.25. Found: 387.27 [M+H]

Example 20

5,6-Bis(4-methylphenyl)-2-(4-benzylpiperazinyl)pyrazine

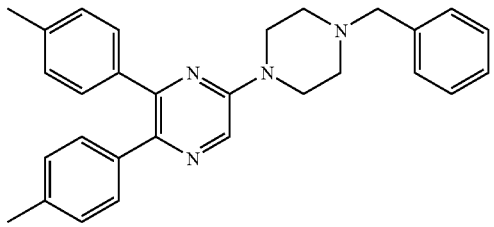

Synthesized according to the method of example 18 to give 7 mg of example 20 as a yellow foam.

Product analytical HPLC: 3.07 min retention time, 93.3% homogeneity index.

$^1$H NMR (CDCl$_3$, 500 MHz) δ 8.41 (s, 1H), 7.51-7.1 (m, 13H), 4.7-4.6 (m, 1H), 4.31 (s, 2H) 3.85-3.5 (m, 2H), 3.0-2.9 (m, 2H), 2.37 (s, 3H), 2.36 (s, 3H). LCMS: Anal. Calcd. for C$_{29}$H$_{30}$N$_4$ 434.25. Found: 435.29 [M+H]

Example 21

5,6-Bis-(4-methylphenyl)-3-methyl-2-piperidinylpyrazine

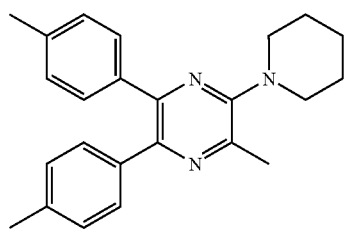

Example 21A

2-Chloro-5,6-bis-(4-methylphenyl)-3-methylpyrazine

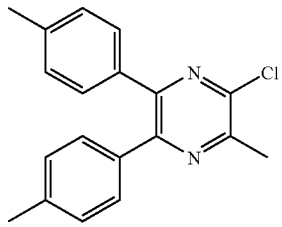

A suspension of L-alanineamide (3.0 g, 24 mmol) and 4,4'-dimethylbenzil (6.9 g, 29 mmol) in 55 mL of 10% aq. MeOH was cooled to −40° C. and a solution of NaOH (2.4 g in 4.8 mL of H$_2$O) was added portionwise over 5 min. The solution was stirred vigorously at −40° C. for 30 min and 16 h at RT. The reaction was quenched with 5 mL of 12 N HCl and the solution was evaporated to dryness to give a solid. The solid was dissolved in 40 mL of POCl$_3$ and conc. H$_2$SO$_4$ (~2 mL) was added until the solution turned to a homogeneous dark red solution. After heating to 105° C. for 16 h, the cooled (RT) solution was poured over 300 mL of ice. The resulting slurry was diluted with 300 mL of ether and the layers were extracted. The aqueous layer was extracted with 200 mL of ether, and the combined organic layers were washed with 300 mL of water then 300 mL of brine. The organic layer was dried over MgSO$_4$, filtered, and evaporated to give a yellow solid that was dissolved in 3 mL of CH$_2$Cl$_4$. The solution was loaded onto dry 120 g silica cartridge and the solvent was evaporated with a stream of nitrogen. The product was eluted with a gradient of 0-25% EtOAc/hexanes to give 0.39 g (5%) of example 21A as an impure yellow solid. HPLC 4.39 min retention time, 61.9% homogeneity index (major impurity, 4,4'-dimethylbenzil: 3.70 min retention time, 17.8% homogeneity index)

Example 21B 5,6-Bis-(4-methylphenyl)-3-methyl-2-piperidinylpyrazine

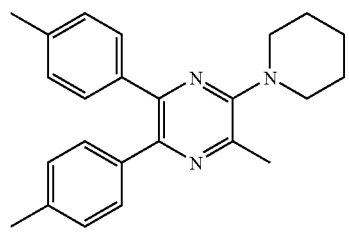

A solution of example 21A (0.15 g, 0.49 mmol) in 1.0 mL of piperidine was stirred for 2 h at room temp then heated to 65° C. for 16 h. The solution was heated to 80° C. for 3 d and the solution was cooled to RT. The reaction solution was evaporated to dryness then redissolved in 4 mL of 90% MeOH/H$_2$O. The product was purified via semi-preparative reverse-phase HPLC to give 0.024 g of example 21B as a yellow oil.

Preparative HPLC Conditions
column: YMC S5 ODS (C-18) 30×100 mm
gradient: 60-100% B over 15 min, hold at 100% B for 3 min.
Solvent A: 10% MeOH/H$_2$O+0.1% TFA
Solvent B: 90% MeOH/H$_2$O+0.1% TFA
Flow rate: 20 mL/min
Monochrome detection at 220 nm.
Product elutes at 16.3 min.

Product analytical HPLC: 4.77 min retention time, 85.0% homogeneity index.

$^1$H NMR (CDCl$_3$, 400 MHz) δ 7.17 (d, 2H, J=8.1 Hz), 7.15-6.99 (m, 4H), 6.95 (d, 2H, J=8.2 Hz), 3.33-3.30 (m, 4H), 2.60 (s, 3H), 2.22 (s, 3H), 2.20 (s, 3H) 1.67-1.58 (m, 6H). HRMS: Anal. Calcd. for C$_{24}$H$_{27}$N$_3$ 357.2205. Found: 358.2293 [M+H]

Example 22

2-Cyclopropylmethylamino-5,6-bis-(4-methylphenyl)-3-methylpyrazine

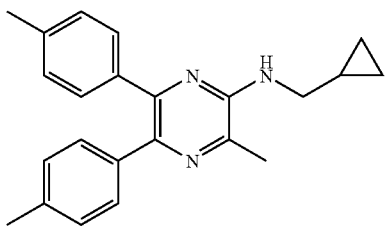

A mixture of cyclopropylmethylamine (0.5 mL), CuI (0.005 g, 0.03 mmol), K$_2$CO$_3$ (0.033 g, 0.24 mmol), pyridine (0.013 mL, 0.16 mmol), DMF (0.5 mL) and example 21A (0.05 g, 0.16 mmol) was heated at 100 C for 16 h. The reaction mixture was cooled to room temp and the solvent was evaporated. The residue was dissolved in 2 mL of 90% MeOH/H2O and was purified via semi-preparative reverse-phase HPLC to give 0.004 g (8%) of 28 as an orange oil.

Semi-preparative HPLC Conditions
Flow rate: 40 mL/min
Solvent A: 10% MeOH–90% H2O–0.1% TFA
Solvent B: 90% MeOH–10% H2O–0.1% TFA
Column: YMC S5 ODS 30×100 mm
Gradient: 0-100% B over 15 min, hold at 100% B for 8 min. product elutes at: 10.8 min.
Analytical HPLC: 4.19 min retention time, 100% homogeneity index.

$^1$H NMR (CDCl$_3$, 400 MHz) δ 7.18-6.96 (m, 8H), 3.36 (d, 2H, J=7.2 Hz), 2.54 (s, 3H), 2.24 (s, 3H), 2.22 (s, 3H), 1.15-1.00 (m, 1H), 0.52 (ddd, 2H, J=1.1, 1.0, 4.8 Hz), 0.22 (m, 2H) LCMS: Anal. Calcd. for C$_{23}$H$_{25}$N$_3$ 343.20. Found: 344.26 [M+H]

Example 23

2-Cyclohexylamino-5,6-bis-(4-methylphenyl)-3-methylpyrazine

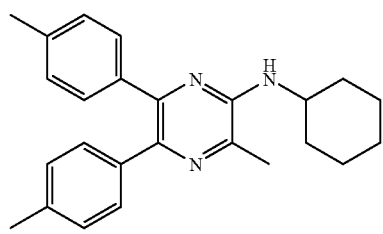

A mixture of cyclohexylamine (0.5 mL), CuI (0.005 g, 0.03 mmol), K$_2$CO$_3$ (0.033 g, 0.24 mmol), pyridine (0.013 mL, 0.16 mmol), DMF (0.5 mL) and example 21A (0.05 g, 0.16 mmol) was heated at 100 C for 16 h. The reaction mixture was cooled to room temp and the solvent was evaporated. The residue was dissolved in 2 mL of 90% MeOH/H2O and was purified via semi-preparative reverse-phase HPLC to give 0.002 g (5%) of example 23 as an orange oil.

Semi-preparative HPLC Conditions
Flow rate: 40 mL/min
Solvent A: 10% MeOH–90% H2O–0.1% TFA
Solvent B: 90% MeOH–10% H2O–0.1% TFA
Column: YMC S5 ODS 30×100 mm
Gradient: 0-100% B over 15 min, hold at 100% B for 8 min. product elutes at: 13.2 min.
Analytical HPLC: 4.46 min retention time, 94.5% homogeneity index.

LCMS: Anal. Calcd. for C$_{25}$H$_{29}$N$_3$ 371.23. Found: 372.45 [M+H]

Example 24

2-Butylamino-5,6-bis-(4-methylphenyl)-3-methylpyrazine

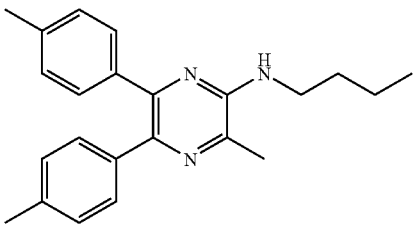

A solution of example 21A (0.07 g, 0.23 mmol), butylamine (0.02 g, 0.28 mmol), Pd$_2$(dba)$_3$ (0.004 g, 0.005 mmol), PPFNMe 0.006 g, 0.014 mmol), and sodium tert-butoxide (0.034 g, 0.35 mmol) in toluene (1.5 mL) was degassed with argon. The reaction solution was heated at 120° C. for 20 min in a microwave. The solution was cooled to room temp, filtered and evaporated. The residue was purified via semi-preparative HPLC (give conditions) to give 0.003 g of example 24 as a yellow oil.

Semi-preparative HPLC Conditions
Flow rate: 40 mL/min
Solvent A: 10% MeOH–90% H2O–0.1% TFA
Solvent B: 90% MeOH–10% H2O–0.1% TFA
Column: YMC S5 ODS 30×100 mm
Gradient: 0-100% B over 15 min, hold at 100% B for 5 min. product elutes at: 13.07 min.
Analytical HPLC: 4.28 min retention time, 95.3% homogeneity index.

$^1$H NMR (CDCl$_3$, 400 MHz) δ 7.27-7.05 (m, 8H), 3.60 (t, 2H, J=7.1 Hz), 2.58 (s, 3H), 2.32 (s, 3H), 2.31 (s, 3H), 1.69-1.65 (m, 2H), 1.46-1.40 (m, 2H), 0.97 (t, 3H, J=7.3 Hz). LCMS: Anal. Calcd. for C$_{23}$H$_{27}$N$_3$ 345.22. Found: 346.29 [M+H].

Biological Evaluation

Cannabinoid Receptor Binding Assay

Radioligand binding studies were conducted in membranes prepared from Chinese Hamster Ovary (CHO) cells that over-express recombinant human CB-1 (CHO-CB-1 cells). Total assay volume for the binding studies was 100 μl.

5 µg of membranes were brought up to a final volume of 95 µl with Binding Buffer (25 mM HEPES, 150 mM NaCl, 2.5 mM CaCl$_2$, 1 mM MgCl$_2$, 0.25% BSA). The diluted membranes were preincubated with a compound or DMSO vehicle. The binding reaction was initiated by the addition of 2 nM final $^3$H-CP-55,940 (120 Ci/mmol) and proceeded for 2.5 hours at room temperature. The binding reaction was terminated by transferring the reaction to GF/B 96 well plates (presoaked with 0.3% polyethylenimine) using a Packard Cell Harvester. The filter was washed with 0.25× PBS, 30 µl MicroScint was added per well, and the bound radiolabel was quantitated by scintillation counting on a Packard TopCount Scintillation Counter. The CB-2 radioligand binding assay was conducted identically except that the membranes from CHO-CB-2 cells were used.

For a compound to be considered a CB-1 antagonist, the compound must possess a CB-1 receptor binding affinity Ki less than 13000 nM. As determined by the assay described above, the CB-1 receptor binding $K_i$ values of working Examples 1-24 fall within the range of 0.01 nM to 13000 nM.

Cannabinoid Receptor Functional Activity Assay

Functional CB-1 inverse agonist activity of test compounds was determined in CHO-CB-1 cells using a cAMP accumulation assay. CHO-CB-1 cells were grown in 96 well plates to near confluence. On the day of the functional assay, growth medium was aspirated and 100 of Assay Buffer (PBS plus 25 mM HEPES/0.1 mM 3-isobutyl-1-methylxanthine/0.1% BSA) was added. Compounds were added to the Assay buffer diluted 1:100 from 100% DMSO and allowed to preincubate for 10 minutes prior to addition of 5 uM forskolin. The mixture was allowed to proceed for 15 minutes at room temperature and was terminated by the addition of 0.1 N HCl. The total intracellular cAMP concentration was quantitated using the Amersham cAMP SPA kit.

Utilities and Combinations

Utilities

The compounds of the present invention are cannabinoid receptor modulators, and include compounds which are, for example, selective agonists, partial agonists, inverse agonists, antagonists or partial antagonists of the cannabinoid receptor. Accordingly, the compounds of the present invention may be useful for the treatment or prevention of diseases and disorders associated with G-protein coupled cannabinoid receptor activity. Preferably, compounds of the present invention possess activity as antagonists or inverse agonists of the CB-1 receptor, and may be used in the treatment of diseases or disorders associated with the activity of the CB-1 receptor.

Accordingly, the compounds of the present invention can be administered to mammals, preferably humans, for the treatment of a variety of conditions and disorders, including, but not limited to metabolic and eating disorders as well as conditions associated with metabolic disorders, (e.g., obesity, diabetes, arteriosclerosis, hypertension, polycystic ovary disease, cardiovascular disease, osteoarthritis, dermatological disorders, hypertension, insulin resistance, hypercholesterolemia, hypertriglyceridemia, cholelithiasis and sleep disorders, hyperlipidemic conditions, bulimia nervosa and compulsive eating disorders) or psychiatric disorders, such as substance abuse, depression, anxiety, mania and schizophrenia. These compounds could also be used for the improvement of cognitive function (e.g., the treatment of dementia, including Alzheimer's disease, short term memory loss and attention deficit disorders); neurodegenerative disorders (e.g., Parkinson's Disease, cerebral apoplexy and craniocerebral trauma) and hypotension (e.g., hemorrhagic and endotoxin-induced hypotension). These compounds could also be used for treatment of catabolism in connection with pulmonary dysfunction and ventilator dependency; treatment of cardiac dysfunction (e.g., associated with valvular disease, myocardial infarction, cardiac hypertrophy or congestive heart failure); and improvement of the overall pulmonary function; transplant rejection; rheumatoid arthritis; multiple sclerosis; inflammatory bowel disease; lupus; graft vs. host disease; T-cell mediated hypersensitivity disease; psoriasis; asthma; Hashimoto's thyroiditis; Guillain-Barre syndrome; cancer; contact dermatitis; allergic rhinitis; and ischemic or reperfusion injury.

Compounds useful in the treatment of appetitive or motivational disorders regulate desires to consume sugars, carbohydrates, alcohol or drugs and more generally to regulate the consumption of ingredients with hedonic value. In the present description and in the claims, appetitive disorders are understood as meaning: disorders associated with a substance and especially abuse of a substance and/or dependency on a substance, disorders of eating behaviors, especially those liable to cause excess weight, irrespective of its origin, for example: bulimia nervosa, craving for sugars. The present invention therefore further relates to the use of a CB-1 receptor antagonist or inverse agonist for the treatment of bulimia and obesity, including obesity associated with type II diabetes (non-insulin-dependent diabetes), or more generally any disease resulting in the patient becoming overweight. Obesity, as described herein, is defined by a body mass index (kg/m$^2$) of at least 26. It may be due to any cause, whether genetic or environmental, including overeating and bulemia, polycycstic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure. As used with reference to the utilities described herein, the term "treating" or "treatment" encompasses prevention, partial alleviation, or cure of the disease or disorder. Further, treatment of obesity is expected to prevent progression of medical covariants of obesity, such as arteriosclerosis, Type II diabetes, polycystic ovary disease, cardiovascular disease, osteoarthritis, dermatological disorders, hypertension, insulin resistance, hypercholesterolemia, hypertriglyceridemia, cholelithiasis and sleep disorders.

Compounds in the present invention may also be useful in treating substance abuse disorders, including substance dependence or abuse without physiological dependence. Substances of abuse include alcohol, amphetamines (or amphetamine-like substances), caffeine, cannabis, cocaine, hallucinogens, inhalents, nicotine, opioids, phencyclidine (or phencyclidine-like compounds), sedative-hypnotics or benzodiazepines, and other (or unknown) substances and combinations of the above. The terms "substance abuse disorders" also includes drug or alcohol withdrawal syndromes and substance-induced anxiety or mood disorder with onset during withdrawal.

Compounds in the present invention may be useful in treating memory impairment and cognitive disorders. The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. Dementias are diseases that include memory loss and additional intellectual impairment separate from memory. Cannabinoid receptor modulators may also be useful in treating cognitive impairments related to attentional deficits, such as attention deficit disorder.

Compounds in the present invention may also be useful in treating diseases associated with dysfunction of brain dopaminergic systems, such as Parkinson's Disease and substance abuse disorders. Parkinsons's Disease is a neurodenerative movement disorder characterized by bradykinesia and tremor.

As modulators of the cannabinoid receptor, the compounds of the present invention are further useful for the treatment and prevention of respiratory diseases and disorders. Respiratory diseases for which cannabinoid receptor modulators are useful include, but are not limited to, chronic pulmonary obstructive disorder, emphysema, asthma, and bronchitis. In addition, cannabinoid receptor modulators block the activation of lung epithelial cells by moeties such as allergic agents, inflammatory cytokines or smoke, thereby limiting release of mucin, cytokines, and chemokines, or selectively inhibiting lung epithelial cell activation.

Moreover, the compounds employed in the present invention may stimulate inhibitory pathways in cells, particularly in leukocytes, lung epithelial cells, or both, and are thus useful in treating such diseases. "Leukocyte activation" is defined herein as any or all of cell proliferation, cytokine production, adhesion protein expression, and production of inflammatory mediators. "Epithelial cell activation" is defined herein as the production of any or all of mucins, cytokines, chemokines, and adhesion protein expression.

Use of the compounds of the present invention for treating leukocyte activation-associated disorders is exemplified by, but is not limited to, treating a range of disorders such as: transplant (such as organ transplant, acute transplant, xenotransplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (asthma, hayfever, allergic rhinitis) or skin allergies; scleracierma; mycosis fungoides; acute inflammatory and respiratory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea. The term "leukocyte activation-associated" or "leukocyte-activation mediated" disease as used herein includes each of the above referenced diseases or disorders. In a particular embodiment, the compounds of the present invention are useful for treating the aforementioned exemplary disorders irrespective of their etiology. The combined activity of the present compounds towards monocytes, macrophages, T-cells, etc. may be useful in treating any of the above-mentioned disorders.

Cannabinoid receptors are important in the regulation of Fc gamma receptor responses of monocytes and macrophages. Compounds of the present invention inhibit the Fc gamma dependent production of TNF alpha in human monocytes/macrophages. The ability to inhibit Fc gamma receptor dependent monocyte and macrophage responses results in additional anti-inflammatory activity for the present compounds. This activity is especially of value, for example, in treating inflammatory diseases such as arthritis or inflammatory bowel disease. In particular, the present compounds are useful for treating autoimmune glomerulonephritis and other instances of glomerulonephritis induced by deposition of immune complexes in the kidney that trigger Fc gamma receptor responses leading to kidney damage.

Cannabinoid receptors are expressed on lung epithelial cells. These cells are responsible for the secretion of mucins and inflammatory cytokines/chemokines in the lung and are thus intricately involved in the generation and progression of respiratory diseases. Cannabinoid receptor modulators regulate both the spontaneous and the stimulated production of both mucins and cytokines. Thus, such compounds are useful in treating respiratory and pulmonary diseases including, COPD, ARDS, and bronchitis.

Further, cannabinoid receptors may be expressed on gut epithelial cells and hence regulate cytokine and mucin production and may be of clinical use in treating inflammatory diseases related to the gut. Cannabinoid receptors are also expressed on lymphocytes, a subset of leukocytes. Thus, cannabinoid receptor modulators will inhibit B and T-cell activation, proliferation and differentiation. Thus, such compounds will be useful in treating autoimmune diseases that involve either antibody or cell mediated responses such as multiple sclerosis and lupus.

In addition, cannabinoid receptors regulate the Fc epsilon receptor and chemokine induced degranulation of mast cells and basophils. These play important roles in asthma, allergic rhinitis, and other allergic disease. Fc epsilon receptors are stimulated by IgE-antigen complexes. Compounds of the present invention inhibit the Fc epsilon induced degranulation responses, including the basophil cell line, RBL. The ability to inhibit Fc epsilon receptor dependent mast cell and basophil responses results in additional anti-inflammatory and anti-allergic activity for the present compounds. In particular, the present compounds are useful for treating asthma, allergic rhinitis, and other instances of allergic disease.

Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

Such other therapeutic agent(s) may be administered prior to, simultaneously with, or following the administration of the cannabinoid receptor modulators in accordance with the invention.

Examples of suitable anti-obesity agents for use in combination with the compounds of the present invention include melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonsist, NPY2 and NPY4 modulators, corticotropin releasing factor agonists, histamine receptor-3 (H3) modulators, aP2 inhibitors, PPAR gamma modulators, PPAR delta modulators, acetyl-COA carboxylase (ACC) inhibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and GB98/284425 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, or cannabinoid-1 receptor antagonists, such as SR-141716 (Sanofi) or SLV-319 (Solvay).

Examples of suitable anti-diabetic agents for use in combination with the compounds of the present invention include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors, SGLT2 inhibitors, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present invention may be employed with a PPARα/γ dual agonist such as MK-767/KRP-297 (Merck/Kyorin; as described in, K. Yajima, et. al., *Am. J. Physiol. Endocrinol. Metab.*, 284: E966-E971 (2003)), AZ-242 (tesaglitazar; Astra-Zeneca; as described in B. Ljung, et. al., *J. Lipid Res.*, 43, 1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Pat. No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No.0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller, et al, *J. Med. Chem.*, 31, 1869-1871 (1998) including isoprenoid (phosphinyl-methyl)phosphonates as well as other known squalene synthetase inhibitors, for example, as disclosed in U.S. Pat. No. 4,871,721 and 4,924,024 and in Biller, S. A., Neuenschwander, K., Ponpipom, M. M., and Poulter, C. D., *Current Pharmaceutical Design*, 2, 1-40 (1996).

In addition, other squalene synthetase inhibitors suitable for use herein include the terpenoid pyrophosphates disclosed by P. Ortiz de Montellano, et al, *J. Med. Chem.,* 20, 243-249 (1977), the farnesyl diphosphate analog A and presqualene pyrophosphate (PSQ-PP) analogs as disclosed by Corey and Volante, *J. Am. Chem. Soc.,* 98, 1291-1293 (1976), phosphinylphosphonates reported by McClard, R. W. et al., *J. Am. Chem. Soc.,* 109, 5544 (1987) and cyclopropanes reported by Capson, T. L., PhD dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SECHOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277, 082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, *Drugs of the Future,* 24, 9-15 (1999), (Avasimibe); "The ACAT inhibitor, C1-011 is effective in the prevention and regression of aortic fatty streak area in hamsters", Nicolosi et al, *Atherosclerosis* (Shannon, Irel), 137 (1), 77-85 (1998); "The pharmacological profile of FCE 27677: a novel ACAT inhibitor with potent hypolipidemic activity mediated by selective suppression of the hepatic secretion of ApoB100-containing lipoprotein", Ghiselli, Giancarlo, *Cardiovasc. Drug Rev.,* 16 (1), 16-30 (1998); "RP 73163: a bioavailable alkylsulfinyl-diphenylimidazole ACAT inhibitor", Smith, C., et al, *Bioorg. Med. Chem. Lett,* 6 (1), 47-50 (1996); "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., *Inflammation: Mediators Pathways,* 173-98 (1995), Publisher: CRC, Boca Raton, Fla.; "ACAT inhibitors: potential anti-atherosclerotic agents", Sliskovic et al, *Curr. Med. Chem.,* 1 (3), 204-25 (1994); "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", Stout et al, *Chemtracts: Org. Chem.,* 8 (6), 359-62 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis* 115, 45-63 (1995) and *J. Med. Chem.* 41, 973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal $Na^+$/bile acid cotransporter inhibitor such as disclosed in Drugs of the Future, 24, 425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin and rosuvastatin, as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and/or T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Cannbinoid receptor modulators could be useful in treating other diseases associated with obesity, including sleep disorders. Therefore, the compounds described in the present invention could be used in combination with therapeutics for treating sleep disorders. Examples of suitable therapies for treatment of sleeping disorders for use in combination with the compounds of the present invention include melatonin analogs, melatonin receptor antagonists, ML 1 B agonists, GABA receptor modulators; NMDA receptor modulators, histamine-3 (H3) receptor modulators, dopamine agonists and orexin receptor modulators.

Cannabinoid receptor modulators may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

Cannibinoid receptor modulators may reduce anxiety or depression; therefore, the compounds described in this application may be used in combination with anti-anxiety agents or antidepressants. Examples of suitable anti-anxiety agents for use in combination with the compounds of the present invention include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present invention include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpah-adrenoreceptor antagonists, and atypical antidepressants (bupropion, lithium, nefazodone, trazodone and viloxazine).

The combination of a conventional antipsychotic drug with a CB-1 receptor antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present invention include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), dipheyylbutylpiperidine (pimozide) and indolone (molindolone) classes of antipsychotic agents. Other antipsychotic agents with potential therapeutic value in combination with the compounds in the present invention include loxapine, sulpiride and risperidone.

Combination of the compounds in the present invention with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, shcizoaffective disorder, delusional disorder, brief psychotic disorder and psychotic disorder not specified. Examples of suitable antipsychotic drugs for combination with the compounds in the present invention include the antipsychotics mentioned above, as well as dopamine receptor antagonists, muscarinic receptor agonists, 5HT2A receptor antagonists and 5HT2A/ dopamine receptor antagonists or partial agonists (e.g., olanzepine, aripiprazole, risperidone, ziprasidone).

The compounds described in the present invention could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and nootropic agents (e.g., piracetam, levetiracetam). Examples of suitable therapies for treatment of Alzheimer's disease and cognitive disorders for use in combination with the compounds of the present invention include donepezil, tacrine, revastigraine, 5HT6, gamma secretase inhibitors, beta secretase inhibitors, SK channel blockers, Maxi-K blockers, and KCNQs blockers.

The compounds described in the present invention could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transportor modulators, such as ropinirole, or pramipexole or neurotrophic factors such as glial derived neurotrophic factor (GDNF).

The compounds described in the present invention could be used in combination with suitable anti-inflammatory agents. Examples of suitable anti-inflammatory agents for use in combination with the compounds of the present invention include prednisone, dexamethasone, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, tumor necrosis factor (TNF) antagonists (e.g., infliximab, OR1384, including TNF-alpha inhibitors, such as tenidap, anti-TNF antibodies or soluble TNF receptor such as etanercept (Enbrel®), rapamycin (sirolimus or Rapamune) and leflunomide (Arava)), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelnorm® and Maxi-K® openers such as those disclosed in U.S. Pat. No. 6,184,231 B1).

Exemplary of such other therapeutic agents which may be used in combination with cannabinoid receptor modulators include the following: cyclosporins (e.g., cyclosporin A), anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), gold compounds, antiproliferative agents such as methotrexate, FK506 (tacrolimus, Prograf), mycophenolate mofetil, cytotoxic drugs such as azathiprine and cyclophosphamide, anticytokines such as antiIL-4 or IL-4 receptor fusion proteins and PDE 4 inhibitors such as Ariflo, and the PTK inhibitors disclosed in the following U.S. patent applications, incorporated herein by reference in their entirety: Ser. No. 09/097,338, filed Jun. 15, 1998; Ser. No. 09/094,797, filed Jun. 15, 1998; Ser. No. 09/173,413, filed Oct. 15, 1998; and Ser. No. 09/262,525, filed Mar. 4, 1999. See also the following documents and references cited therein and incorporated herein by reference: Hollenbaugh, D., Et Al, "Cleavable CD40Ig Fusion Proteins and the Binding to Sgp39", *J. Immunol. Methods* (Netherlands), 188 (1), pp. 1-7 (Dec. 15, 1995); Hollenbaugh, D., et al, "The Human T Cell Antigen Gp39, A Member of the TNF Gene Family, Is a Ligand for the CD40 Receptor: Expression of a Soluble Form of Gp39 with B Cell Co-Stimulatory Activity", *EMBO J* (England), 11 (12), pp. 4313-4321 (December 1992); and Moreland, L. W. et al., "Treatment of Rheumatoid Arthritis with a Recombinant Human Tumor Necrosis Factor Receptor (P75)-Fc Fusion Protein," *New England J. of Medicine,* 337 (3), pp. 141-147 (1997).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of formula (I) of the invention can be administered orally or parenterally, such as subcutaneously or intravenously, as well as by nasal application, rectally or sublingually to various mammalian species known to be subject to such maladies, e.g., humans, in an effective amount up to 1 gram, preferably up to 200 mg, more preferably to 50 mg in a regimen of single, two or four divided daily doses.

The compounds of the formula (I) can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula (I) can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:

1. A compound according to Formula I

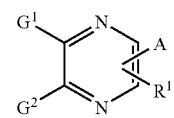

including all pharmaceutically acceptable salts and stereoisomers, wherein:

$G^1$ and $G^2$ are independently selected from the group consisting of aryl or heteroaryl wherein heteroaryl is selected from the group consisting of isooxazole,

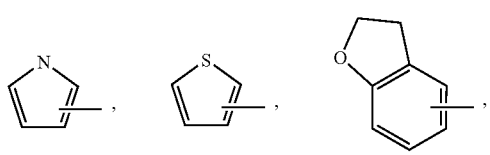

-continued

[structures]

A is C(O)NR²R³;
R¹ is selected from the group consisting of hydrogen, halogen, OH, CN, alkyl, aryl and heteroaryl;
R³ is hydrogen;
R² is selected from the group consisting of substituted alkyl, substituted cycloalkyl, alkoxy, C(O)R¹⁰, iminoalkyl, S(O)R⁸ and S(O)₂R⁸, wherein
alkyl is substituted with one or more members selected from the group consisting of alkenyl, alkynyl, hydroxyl, alkoxyl, arylalkyloxy, heteroaryloxy, heteroarylalkyloxy, heterocyclyl, alkanoyl, halo, haloalkyl, thio, alkylthio, nitro, cyano, carboxyl, carbalkoyl, carboxamido, alkylamino, dialkylamino, amido, arylamido, heteroarylamido, azido, guanidino, amidino, phosphonic, phosphinic, sulfonic, sulfonamido, CF₃, OCF₃, aryloxy, cycloalkylalkoxyalkyl, and cycloheteroalkyl;
wherein cycloalkyl is substituted with one or more members selected from the group consisting of haloalkyl, alkyl, alkoxy, haloalkoxy, alkenyl, trifluoromethyl, trifluoromethoxy, alkynyl, cycloalkylalkyl, fluorenyl, heterocycloalkyl, heterocycloalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, nitro, oxo, cyano, carboxamido, amido, azido, guanidino, amidino, phosphonic, phosphinic, sulfonic, sulfonamide, thiol, alkylthio, arylthio, heteroarylthio, arylthioalkyl, alkoxyarylthio, alkylcarbonyl, arylcarbonyl, alkylaminocarbonyl, arylaminocarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl;
R⁸ is selected from the group consisting of alkyl, cycloalkyl, aminoalkyl, aminocycloalkyl, aminoheterocyclyl, aminoaryl, aminoheteroaryl, heterocyclyl and aryl; and
R¹⁰ is selected from the group consisting of alkyl, aryl, heteroaryl, and alkoxy.

2. A compound according to Formula I

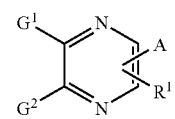

including all pharmaceutically acceptable salts and stereoisomers, wherein:
G¹ and G² are independently selected from the group consisting of aryl and heteroaryl;
A is C(O)NR²R³;
R¹ is selected from the group consisting of hydrogen, halogen, OH, CN, alkyl, aryl and heteroaryl;
R² is alkyl which is substituted by at least one member selected from the group consisting of alkenyl, alkynyl, hydroxyl, alkoxyl, arylalkyloxy, heteroaryloxy, heteroarylalkyloxy, alkanoyl, halo, haloalkyl, thio, alkylthio, nitro, cyano, carboxyl, carbalkoyl, carboxamido, amido, azido, guanidino, amidino, sulfonamido, CF₃, OCF₃, aryloxy and a heteroaryl group that is fused to another aryl and heteroaryl group; or
R² is cycloalkyl which is substituted by at least one member selected from the group consisting of alkenyl, alkynyl, alkoxyl, arylalkyloxy, heteroaryloxy, heteroarylalkyloxy, alkanoyl, haloalkyl, thio, alkylthio, nitro, cyano, carbalkoyl, carboxamido, aminoaryl, amido, azido, guanidino, amidino, sulfonamido, CF₃, OCF₃, aryloxy and a heteroaryl group that is fused to another aryl and heteroaryl;
R³ is selected from hydrogen, alkyl, heterocyclyl, alkoxy, heteroaryl, C(O)R¹⁰, aminoalkyl and iminoalkyl; and
R¹⁰ is selected from the group consisting of alkyl, aryl, heteroaryl, and alkoxy.

3. The compound according to either of claim 1 or 2, wherein G¹ and G² are aryl substituted with 1 or more members selected from the group consisting of hydrogen, alkyl, halo, haloalkyl, alkoxy, haloalkoxy, alkenyl, trifluoromethyl, trifluoromethoxy, alkynyl, cycloalkylalkyl, fluorenyl, heterocycloalkyl, heterocycloalkylalkyl, aryl, heteroaryl, arylalkyl, aryloxy, aryloxyalkyl, arylalkoxy, arylthio, arylazo, heteroarylalkyl, heteroarylalkenyl, heteroaryloxy, heteroarylalkyloxy, heteroarylalkyloxyalkyl, hydroxy, nitro, oxo, cyano, amino, substituted amino wherein the amino includes 1 or 2 substituents (which are alkyl, cycloalkyl, heterocycloalkyl, heteroaryl, or aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, cycloalkylaminocarbonyl, arylaminocarbonyl, heteroarylaminocarbonyl, heteroarylalkylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl.

4. The compound according to claim 3, wherein G¹ and G² are each

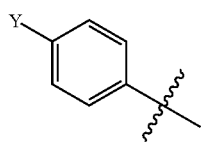

wherein Y is selected from the group consisting of methyl and chloro.
5. The compound according to either of claims 1 or 2, wherein the compound is selected from
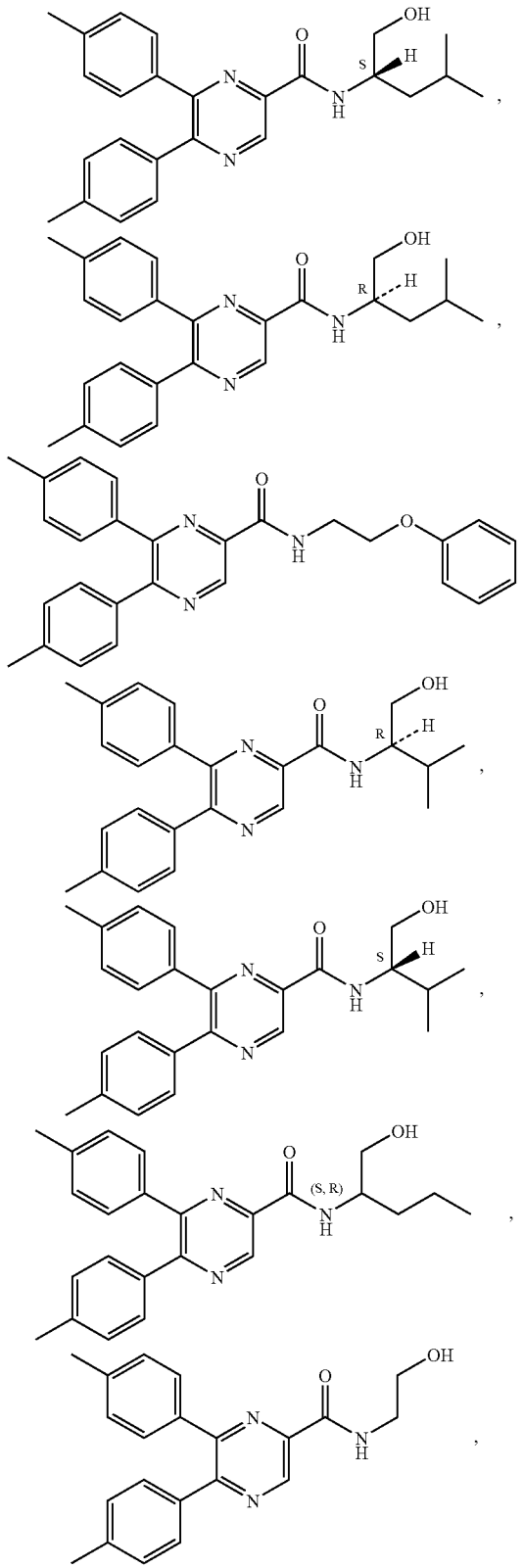
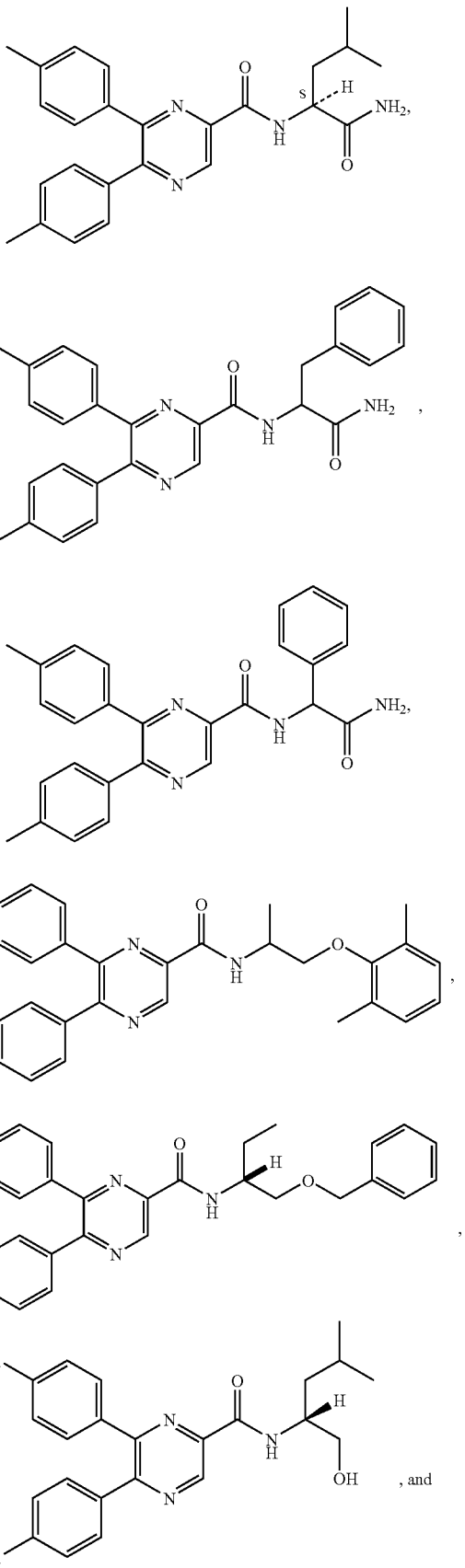

-continued

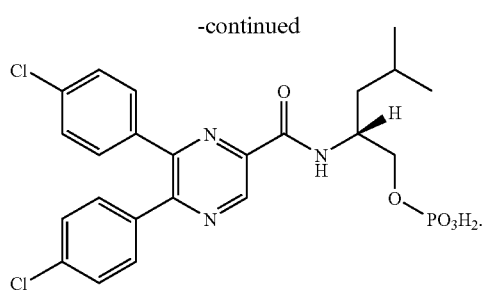

6. A pharmaceutical composition comprising at least one compound according to any one of claims 1, 2 and 3 to 5 and a pharmaceutically acceptable carrier or diluent.

7. A method for the treatment of obesity or bulimia, which comprises administering to a mammalian species in need of treatment a therapeutically effective amount of a compound as defined in either of claim 1 or claim 2.

* * * * *

UNITED STATES PATENT AND TRADEMARK OFFICE
CERTIFICATE OF CORRECTION

PATENT NO. : 7,326,706 B2 Page 1 of 1
APPLICATION NO. : 10/917199
DATED : February 5, 2008
INVENTOR(S) : Bruce A. Ellsworth, Chongqing Sun and Annapurna Pendri It is certified that error appears in the above-identified patent and that said Letters Patent is hereby corrected as shown below:

Claim 5, column 45, line 3, please delete "claims" and insert -- claim --.

Signed and Sealed this

Twelfth Day of August, 2008

JON W. DUDAS
*Director of the United States Patent and Trademark Office*